United States Patent [19]
Salahuddin et al.

[11] Patent Number: 6,018,027
[45] Date of Patent: Jan. 25, 2000

[54] HUMAN HERPESVIRUS-6 (HHV-6) ISOLATION AND PRODUCTS

[75] Inventors: Syed Zaki Salahuddin, Rockville; Dharam V Ablashi, Olney; Steven F. Josephs, Rockville; Carl W. Saxinger, Bethesda; Flossie Wong-Staal, Rockville; Robert C. Gallo, Bethesda, all of Md.

[73] Assignee: The United States of America as represented by the Department of Health and Human Services, Washington, D.C.

[21] Appl. No.: 09/000,854

[22] Filed: Dec. 30, 1997

Related U.S. Application Data

[62] Division of application No. 08/774,118, Dec. 23, 1996, which is a division of application No. 08/392,674, Feb. 22, 1995, Pat. No. 5,604,093, which is a continuation of application No. 07/754,220, Aug. 27, 1991, abandoned, which is a continuation of application No. 07/255,712, Oct. 11, 1988, abandoned, which is a continuation-in-part of application No. 07/228,550, Aug. 4, 1988, abandoned, which is a continuation-in-part of application No. 06/901,602, Aug. 29, 1986, abandoned, which is a continuation-in-part of application No. 06/892,423, Aug. 4, 1986, abandoned, which is a continuation-in-part of application No. 06/895,857, Aug. 12, 1986, abandoned, which is a continuation-in-part of application No. 06/895,463, Aug. 11, 1986, abandoned.

[51] Int. Cl.⁷ .................................................... C07K 14/03
[52] U.S. Cl. ................................................ 530/350; 435/5
[58] Field of Search .............................. 435/5; 530/350

[56] References Cited

U.S. PATENT DOCUMENTS 4,237,224  12/1980  Cohen et al. .
4,994,386  2/1991   Hung .
5,230,997  7/1993   Frenkel .

FOREIGN PATENT DOCUMENTS 8400979  3/1984  WIPO .

OTHER PUBLICATIONS

Albashi et al., "HBLV (or HHV–6) in human cell lines)", *Nature* vol. 329, No. 6136 (Sep. 1987) p. 1723.

Lusso et al., "In vitro Cellular Tropism of Human B–Lymphotropic Virus . . . ", *J. Exp Med.* vol. 167 (May 1988) pp. 1659–1670.

Rodriquez et al., Recombinant DNA Techniques: An Introduction, (published 1983), pp. 74–76.

Josephs et al., "Genomic analysis of the human B–Lymphotropic virus", *Science*, vol. 24, pp. 601–603 (1986).

Lawrence et al., Human Herpesvirus 6 Is Closely Related to Human Cytomegalovirus. J. Virol. 64(1):287–299, 1990.

Frankel–Conrat et al., *Virology*, Prentice–Hall, Englewood, N.J., 1982, pp. 207–211.

Barnes, "Mystery Disease At Lake Tahoe Challenges Virologists and Clinicans", *Science* 234:542, 1986.

*Primary Examiner*—Donna Wortman
*Attorney, Agent, or Firm*—Townsend and Townsend and Crew LLP

[57] ABSTRACT

A new human B lymphotropic virus, also designated human herpesvirus-6, has been isolated. DNA, molecular clones, antigenic viral proteins and antibodies having specificity to the new virus have been prepared. Various utilities of the new virus and products derived therefrom have been described.

3 Claims, 18 Drawing Sheets

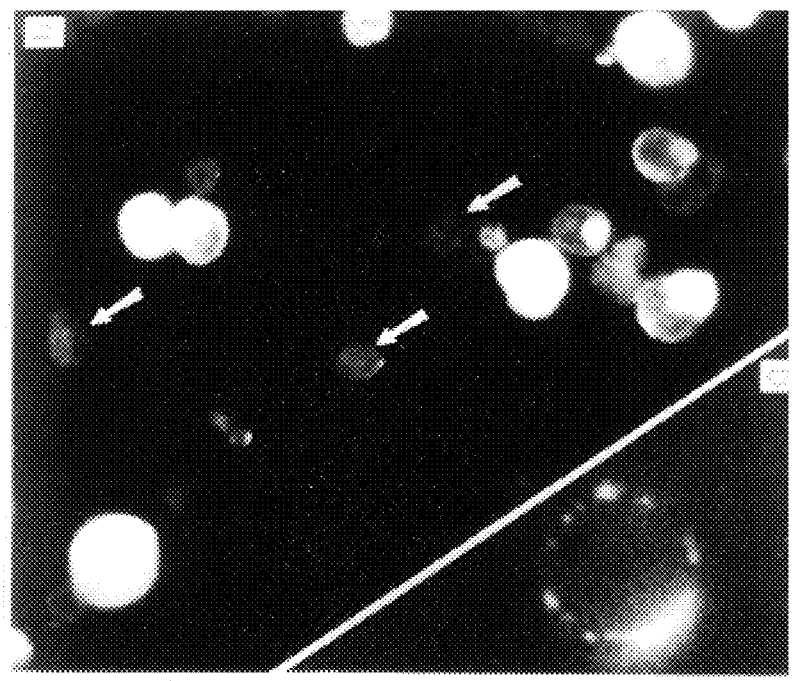
FIG. 2A.
FIG. 2B.
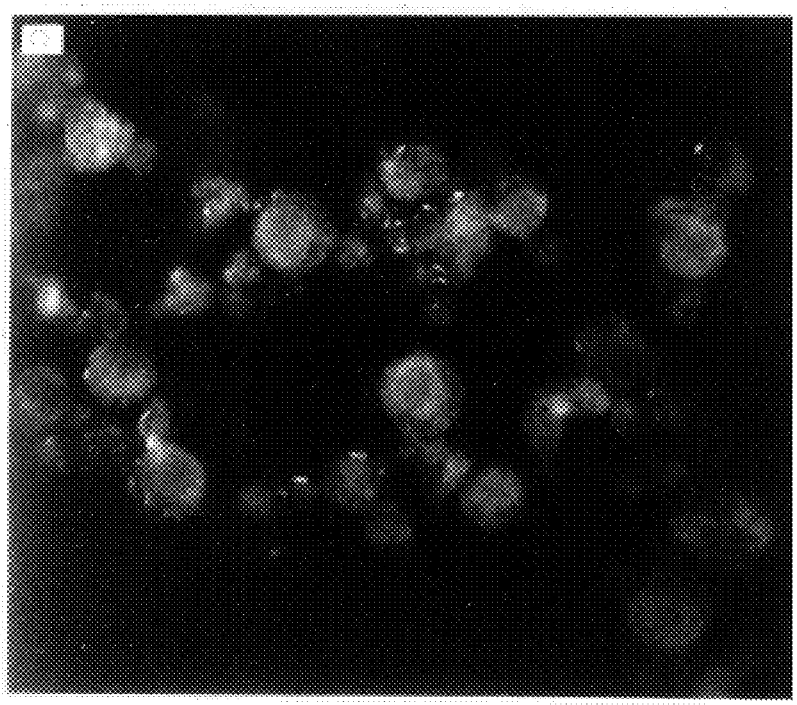
FIG. 2C.

HUMAN B-LYMPHOTROPIC VIRUS (HBLV)

HYBRIDIZATION OF HHV-6 SPECIFIC CLONE. ZVH-14 TO DNA FROM HBLV INFECTED CORD BLOOD LYMPHOCYTES.

A=Hind-III            B=Eco-RI

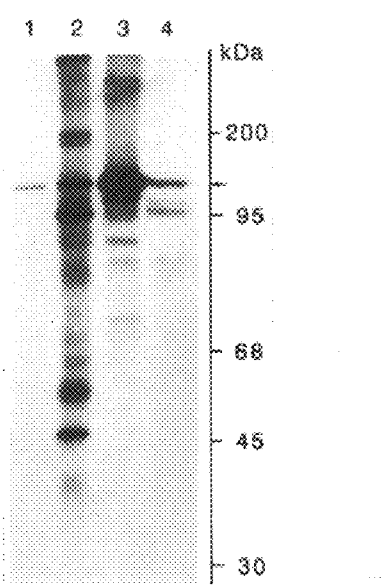

3 hrs ³⁵S Methionine and ³⁵S cysteine labeled HSB-2 infected cells.
Lane 1. HBLV negative serum by IFA
Lane 2. Rabbit HBLV hyperimmune serum
Lane 3. HBLV high positive serum by IFA from CFS patient
Lane 4. HBLV low positive serum by IFA

FIG. 7A.

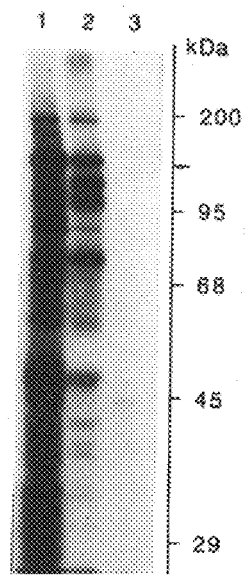

HBLV positive serum by IFA reacted with
Lane 1. 15 hrs labeled - HBLV infected HSB-2 cell supernatant
Lane 2. infected cells (HSB-2) lysates.
Lane 3. Uninfected cells (HSB-2) lysates.

≈120 kDa consistantly recognized in HBLV positive sera

WESTERN BLOT ANALYSIS OF HBLV PROTEINS

A = Concentrated HBLV from HSB-2 Cells

B = HSB-2 Cell Lysates

Lane 1 and 2: HBLV Antibody Positive Sera

Lane 3: HBLV Antibody Negative Serum

HBLV Sequences in a follicular Large cell Lymphoma.

LANE 1 — Negative Control
LANE 2 — Tumor Cell DNA
LANE 3 — DNA from HBLV positive BL DNA from negative and positive controls and Tumor (Lane 2) was digested with EcoR-1.

LANE 1 ABDOMINAL NODE
LANE 2 THORACIC NODE
LANE 3 PERIPHERAL BLOOD LYMPHOCYTES
LANE 4 LIVER
LANE 5 EARLY SALIVARY GLAND BIOPSY

FIG. 13A. ETHIDIUM BROMIDE STAIN

FIG. 13B. HYBRIDIZATION OF 2 AND 3 RESPECTIVELY TO HBLV PROBE pZVH14

HUMAN HERPESVIRUS-6 (HHV-6) ISOLATION AND PRODUCTS

This application is a divisional of and claims the benefit of U.S. application Ser. No. 08/774,118, filed Dec. 23, 1996, which was a divisional of Ser. No. 08/392,674, filed Feb. 22, 1995, now U.S. Pat. No. 5,604,093, which was a continuation of Ser. No. 07/754,220, filed Aug. 27, 1991, now abandoned, which was a continuation of Ser. No. 07/255, 712, filed Oct. 11, 1988, now abandoned, which was a CIP of Ser. No. 07/228,550, filed Aug. 4, 1988, now abandoned, which was a CIP of Ser. No. 06/901,602, filed Aug. 29, 1986, now abandoned, which was a CIP of Ser. No. 06/892,423, filed Aug. 4, 1986, now abandoned, which was a CIP of Ser. No. 06/895,857, filed Aug. 12, 1986, now abandoned, which was a CIP of Ser. No. 06/895,463, filed Aug. 11, 1986, now abandoned, the disclosure of which is incorporated by reference.

The present invention is related generally to the isolation and characterization of a new virus. More particularly, the present invention is related to providing a biologically pure, isolated human B lymphotropic virus, molecular clones, nucleic acid, distinctive antigenic proteins and a method for detecting antibodies to the new virus. A virus of the type as described herein has not heretofore been known or characterized. The nature, properties, importance and various utilities of the new virus are now presented.

A virus, designated as human B-lymphotropic virus (HBLV or HHV-6 for human herpesvirus-6 ), was isolated from the peripheral blood lymphocytes of six individuals: one HTLV-III(HIV-1 ) seropositive patient with AIDS-related syndrome, 1 HTLV-III seropositive patient with angio-immunoblastic lymphadenopathy, 1 patient with dermatopathic, a patient with Mycosis fungoides, a patient with immunoblastic lymphoma, and 1 patient (GS) with acute lymphoblastoid leukemia (Table 1). All six isolates were closely related by antigenic and molecular analysis, and sera from all 6 virus positive patients reacted immunologically with each virus isolate (Table 1). In contrast, only 4 sera from more than 200 randomly selected healthy donors were seropositive. Subsequent tests showed a high number of normal blood donors had titers to HHV-6 (59.5%). It was found that HBLV contains a large double-stranded DNA genome, and is morphologically similar to some members of the human herpesvirus group. A detailed morphological analysis of HBLV is given below.

It selectively infects freshly isolated human umbilical cord blood lymphocytes, B-cells and T cells, where it induces the appearance of characteristic large, refractile mononucleated or binucleated cells containing nuclear and cytoplasmic inclusions bodies. HBLV is distinguishable from all known human and sub-human primate herpesviruses by host range, biological effect on infected cells, and by a lack of immunologic, antigenic and genomic relatedness (Tables 2 and 3).

Despite morphological similarities, the host range of HBLV was different from all other members of the human herpesvirus group. For example, initial attempts to transmit the virus to a number of T and B lymphoblastoid cell lines, and to a variety of other cell types, were unsuccessful, but later tests showed that B- and T-cells, megakaryocytes and neural cells could be infected with HBLV. In contrast, Epstein-Barr virus (EBV) infects most B cells and some epithelial cells. Furthermore, other herpesviruses [e.g., cytomegalovirus (CMV), Herpes Simplex I and II (HSV) and Varicella-Zoster virus (VZV), infect a variety of cell types, often inducing cytopathic effects. Immunological comparisons with EBV further emphasized these differences. For example, no EBV nuclear antigens were detected in HBLV-infected cord blood mononuclear cells.

The virus of the present invention has been designated human B-lymphotropic virus (HBLV) because the virus was intially cultured from B-cells (the cells had cytoplasmic immunoglobulins), because the virus initially infects B-cells in vitro in cord blood cultures and because HBLV DNA sequences were found in only 3 lymphomas and all 3 were of B-cell origin. Comparative morphological features which distinguish HBLV from other human herpesviruses are listed in Table 4.

For the identification and isolation of HBLV, fresh peripheral blood mononuclear cells from AIDS patients with associated lymphoproliferative disorders were established in cell culture (Table 1). In the cultures of eight patients, primary cell cultures contained a small number of large, refractile mononucleated or binucleated cells which survive for short periods of time. These cells frequently contained intranuclear and/or intracytoplasmic inclusion bodies. Electron microscope examination revealed that these cells were infected by a DNA virus, 200 nm in diameter (FIG. 3). These large cells were also the only ones in culture expressing viral antigens, as measured by fixed and unfixed cell indirect immunofluorescence assays (IFA) (FIG. 2) and by in situ hybridization (FIG. 1). All three virus-positive patients were homosexual males (2 white and 1 black, between the ages of 35 and 44), who were seropositive for HTLV-III with AIDS-pneumocystic pneumonia, with Kaposi's sarcoma, and with undifferentiated B-cell lymphoma.

The presence of the unique large, refractile cells suggested the need for further examination of patients demonstrating morphologically similar cells in fresh tissues or culture.

HBLV from all six patients could be transmitted to freshly isolated human leukocytes from umbilical cord blood, adult peripheral blood, bone marrow, and spleen (previously stimulated with PHA-P (phytohemagglutinin-purified)). After in vitro infection the large refractile cells, noted in primary cultures, appeared within 2–4 days post infection. These cells eventually became the predominant cells in the culture, surviving for an additional 8–12 days. During this time the other cells in the culture rapidly died. As in primary cell cultures, these large cells expressed viral nucleic acids as shown by in situ hybridization (FIG. 1), and viral antigens as detected by IFA (immunofluorescent antibodies) (FIG. 2). Virus production was confirmed by electron microscopy (FIG. 3). HBLV-infected cells were typed for surface markers defined by specific monoclonal antibodies.

Molecular probes which were derived from HSV-1 (cross reactive with HSV-2), CMV, EBV and VZV were used for comparisons with HBLV. While each individual viral probe hybridized to its homologous nucleic acids, HBLV was clearly distinct from these human herpesviruses (FIG. 10). Furthermore, the size of the HBLV genome was shown to contain a minimum complexity of 110 kb-pair as determined by analysis of sucrose gradient purified viral DNA. Finer analysis indicates the genomic size to be about 170 kb. This genome size, as well as other features (such as morphology), also distinguished HBLV from DNA viruses of the adenovirus, polyomavirus, papovavirus, and papillomavirus groups.

BRIEF DESCRIPTION OF THE DRAWINGS

FIG. 2A is an immunofluorescent analysis of HBLV-infected acetone fixed cells;

FIG. 2B shows HBLV-infected live cells expressing membrane fluorescence using HBLV antibody; and FIG. 2C shows immunofluorescence of HBLV-infected cells with serum lacking HBLV antibody.

FIG. 5A: Hind III digested HBLV genomic DNA.

FIGS. 7A and B show the one dimensional (1D) gel electrophoresis patterns of proteins recognized by human and rabbit anti-HBLV serum by radioimmunoprecipitation. FIG. 7A: 3 hrs $^{35}$S Cysteine labeled HSB-2 infected cells. FIG. 7B: Identification of 120 kd protein using HBLV positive serum.

FIG. 8 shows restriction enzyme map of HBLV clone pZVH14.

FIG. 9A: Concentrated HBLV from HSB 2 cells.

FIG. 11A: HBLV sequences in a follicular large cell lymphoma.

FIG. 13A: Ethidium Bromide Straining.

FIG. 16 is a map of HBLV clone pZVB70.

Figure 1:
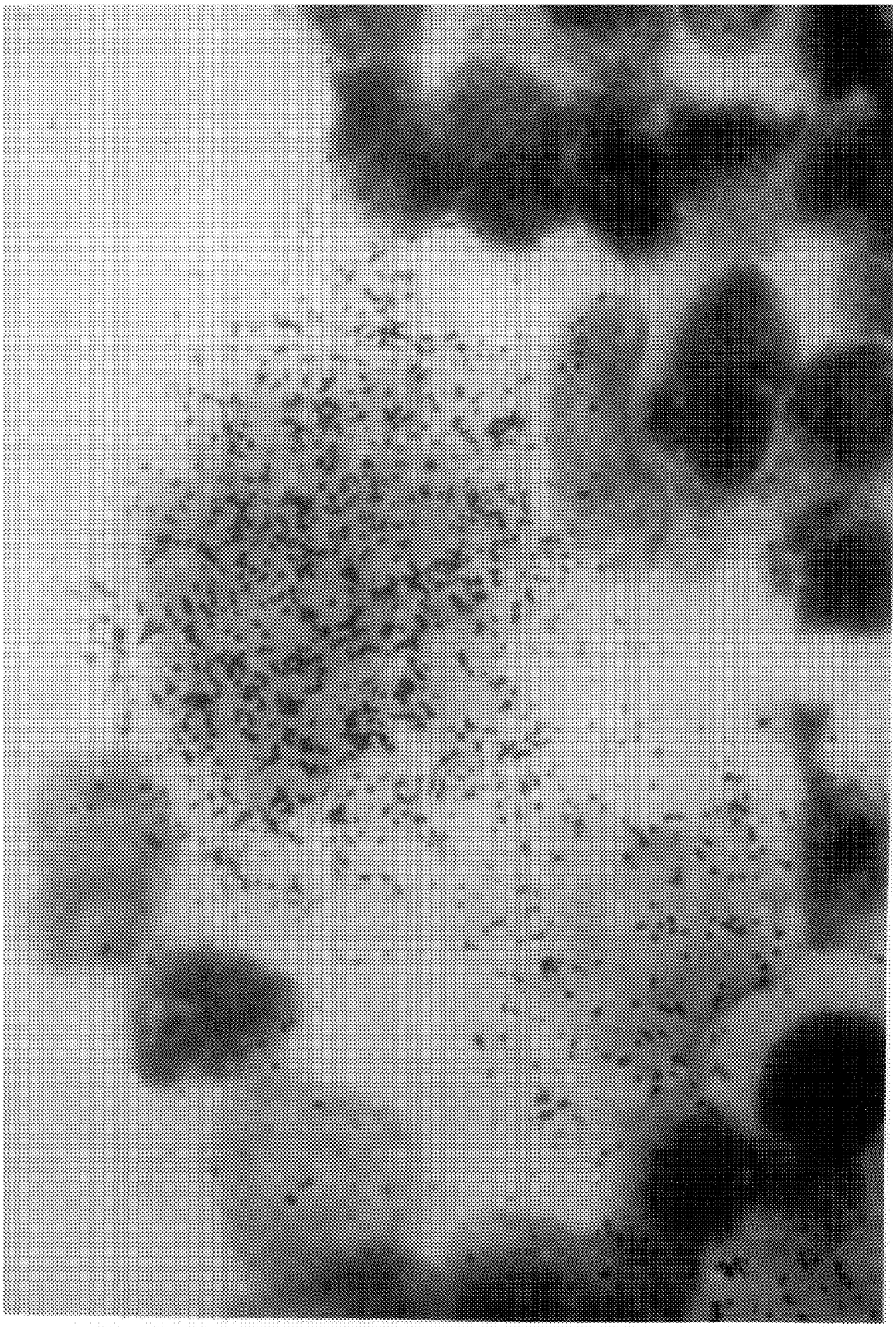
FIG. 1 shows the results of in situ hybridization of HBLV-infected human cord blood cells using pZVH14 HBLV probe.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

The term "substantially pure" as used herein means that the product is as pure as can be obtained by standard methodology conventional in the art.

Despite morphological and other properties similar to some of the herpesviruses, human B lymphotropic virus (HBLV) is a new human herpesvirus. It is distinguishable from other viruses by biological properties and by the lack of immunological and genomic homology. HBLV is highly lytic in vitro, as are CMV, HSV, HVS (Herpesvirus simia), and HVA (Herpesvirus ateles), but has a different host range than these viruses. It is possible that HBLV could indirectly cause abnormalities in B-cells leading to malignancy in vivo.

Even though in certain instances HBLV was associated with human T-lymphotropic virus-III/lymphadenopathy-associated virus (HTLV-III/LAV) seropositive donors, other evidence indicates that it is not exclusively an AIDS-associated agent. Not only did all HTLV-III seropositive patients have complicating lymphoproliferative disorders, but HBLV was also isolated from a HTLV-III seronegative ALL (acute lymphocytic leukemia) patient. Furthermore, some seroepidemiological analyses have shown a reactivity clearly dissociated from HTLV-III antibody positive individuals.

Serological comparisons demonstrate the uniqueness of HBLV. Immunofluorescence assay was developed following techniques originally described for herpesviruses, and was used to analyze patients and healthy control sera, and to monitor infected cells. Sera from all six HBLV positive patients demonstrated an IgG antibody titer to viral capsid antigens (>1:20). In contrast, only 4 of the more than 200 sera from randomly selected healthy donors were positive. Subsequent serological surveys indicate the prevalence of HBLV antibodies in normal population to range from about 9% to about 47% with regional differences. The pattern of immunofluorescent staining in fixed, infected cells varied from punctate nuclear staining to diffuse staining of the entire cell (FIG. 2A). In live cells, the staining was confined to the cell membrane either as a partial ring or in a capped form (FIGS. 2B and C). Uninfected cord blood mononuclear cells were negative when tested with sera from the 6 HBLV positive patients. Sera from these positive patients also contained antibody to EBV and CMV. A careful comparison of the titers of antibody to EBV, CMV, and HBLV yielded a distinct titer for HBLV as compared to that for EBV and CMV. Furthermore, the reactivity to EBV, CMV, HSV-1 and 2 and VZV was completely removed by adsorption with disrupted, EBV-infected cells or with purified viruses, without significantly affecting the antibody titer to HBLV.

Sucrose gradient purification of HBLV. Heparinized peripheral blood leukocytes or human umbilical cord blood mononuclear cells are banded in Ficoll-Hypaque and established in cell culture at 36° C. following PHA-P (5ug/ml) stimulation for 48 hours. The cells are then grown in RPMI-1640 medium supplemented with 10% fetal bovine serum (heat inactivated, 56° C. for 30 min.) and 5ug/ml hydrocortisone. Frozen supernatants obtained from the infected cells are thawed, collected in 250 ml tubes and spun at 3500 rpm in a Sorvall GSA rotor at 5° C. for 10 min. The clarified supernatants are transferred to SW28 tubes and spun and pelleted at 17,000 rpm for 90 min. at 5° C. Pellets obtained are resuspended in 10 mM Tris-HCl pH 7.4, 10 mM NaCl, 1 mM EDTA (TNE) to a volume of 300 microliters and layered onto a 15–60% sucrose gradient and spun in an SW41 rotor (Beckman) at 20,000 rpm for 30 min. at 5° C. Fractions of 1 ml are collected from the top of the gradient. Each fraction is diluted to 10 ml, spun, and pelleted in an SW41 rotor at 17,000 rpm for 90 min. Pellets are resuspended in 300 microliters of TNE and aliquots assayed (by ELISA and Western Blot) for the presence of virus and for virus infectivity. Human B Lymphotropic Virus is easily detected in fractions 4–9 with a peak in fractions 5–7 by both assays. Extraction of nucleic acids from each fraction shows the presence of double stranded DNA in fractions 5–9 with a peak in fraction 7. Virus is also detected by electron microscopy in the SW41 gradient pellet as well. Virus purified from fresh unfrozen supernatants according to this procedure is used for detailed electron microscopy.

Aliquots of the sucrose gradient fractions can be definitively assayed for the presence of HBLV by DNA dot blot analysis using the pZVH14 9 kb insert (FIG. 8) as a probe. The pZVH14 molecular clone is obtainable from the American Type Culture Collection under Accession No. 40247.

The immunofluorescence, Western blot and radioimmuno-precipitation assays are also employed for detecting HBLV infection and HBLV antibodies in a variety of hematopoietic malignancies, including B-cell lymphomas of both AIDS and non-AIDS origin. The presence of HBLV antibodies is elevated in the following disease groups, but the invention is not intended to be limited to these specific diseases:

Roseola (Exanthum subitum)

Burleitt's lymphoma

Hodgkin's disease

Mononucleosis-like syndromes

Sarcoidosis

Sjogren's Syndrome

A newly described infectious disease syndrome similar to that seen in Lake Tahoe characterized as an "acute mononucleosis-like syndrome" in adults, commonly known as chronic fatigue syndrome (CFS).

ALL (acute lymphocytic leukemia) as diagnosed in children of Japanese, Caribbean and African origin.

HIV-1 antibody positive AIDS, ARC and PGL (persistent generalized lymphadenopathy) patients.

HBLV Virus Propagation. Infection of human umbilical cord blood or peripheral blood mononuclear cells is conducted by cell-free transmission as follows:

1) Fresh blood samples are diluted 1:1 with RPMI-1640 and spun (and banded) on a Ficoll gradient.

2) The banded mononuclear cells are washed and put into culture in the presence of PHA-P (5ug/ml) and hydrocortisone (HC) (5ug/ml) in 20% fetal calf serum (FCS) and RPMI-1640.

3) After 24 hours, polybrene (2ug/ml) is added to the culture and after 6–24 hours, the cells are pelleted.

4) A one ml aliquot of freshly harvested or frozen infected culture supernatant is added to the pellet and incubated at 37° C. for 1–2 hour, with frequent agitation.

5) Fresh medium [10% FCS and HC (5ug/ml) in RPMI-1640] is then added to the suspension, cultured, and incubated at 36° C.

6) Within 2–10 days post infection, the characteristic enlarged refractile cells become visible. Supernatant is harvested at the peak of infection as measured by immunofluorescence and by visual observation of the culture for further transmission.

Cells infected by HBLV were also used to directly compare immunological cross-reactivities with other human and nonhuman primate herpesviruses using specific monoclonal antibodies, hyperimmune sera, or sera from antibody positive control donors. As summarized in Tables 2 and 3, monoclonal antibodies to EBV, CMV, HSV, and hyperimmune sera to Rhesus CMV and African Green CMV, did not react with HBLV-infected cells. Human sera possessing antibodies to EBV, CMV, HSV, and VZV also did not react with HBLV-infected cells. Furthermore, sera from several old World and New World primates, many of which had antibodies to nonhuman primate herpesvirus (including EBV-like viruses and CMV), did not show any cross-reactivity with HBLV-infected cells (Table 2).

Immunofluorescent Analysis of HBLV-infected cells. A modification of the indirect immunofluorescence assay developed by Henle et al (J. Bacteriol.91:1248–1256) for EBV was used for the detection of antibody to HBLV capsid antigens. For this assay, HBLV-infected cord blood mononuclear cells were isolated by Ficoll gradients to remove dead cells. Uninfected human cord blood mononuclear cells were used as controls. Uninfected and infected cells were washed 3 times for 10 minutes with PBS without Mg++ Ca++, resuspended in PBS containing Mg++Ca++, deposited on Teflon coated slides, air dried, and fixed in cold acetone for 10 minutes. Patient's sera (heat inactivated at 56° C. for 30 minutes and clarified by centrifugation) were added to the acetone fixed cells, incubated in a humidity chamber at 37° C. for 40 minutes, washed with PBS, air dried, and stained with affinity purified FITC conjugated anti-human IgG (H and L) for 40 minutes. The cells were counterstained with Evans blue (1:500 dilution in PBS) for 5 min to further reduce background due to autofluorescence. The cells were again washed as above, air dried, and mounted with IFA (immunoflourecence assay) mounting solution. Large cells with greenish to yellow granular immunofluorescent and cytoplasmic staining were scored as positive cells for HBLV. The example of assays carried out 5 days post infection are shown in FIG. 2a. Small cells in the background did not react with patient serum (FIG. 2b with arrows).

As is shown in FIG. 2, detection of viral membrane antigen HBLV infected as well as uninfected live cells (non-fixed) were washed 3 times in serum-free RPMI1640 medium and treated with patient's serum for 30 minutes at 4° C. The cells were again washed, treated with affinity purified FITC anti-human IgG for another 30 minutes, washed in medium again and examined for membrane fluorescence. HBLV infected cells showed surface markers when tested with patient serum using the immunofluorescence technique (FIG. 2b).

Figures 5A, 5B:
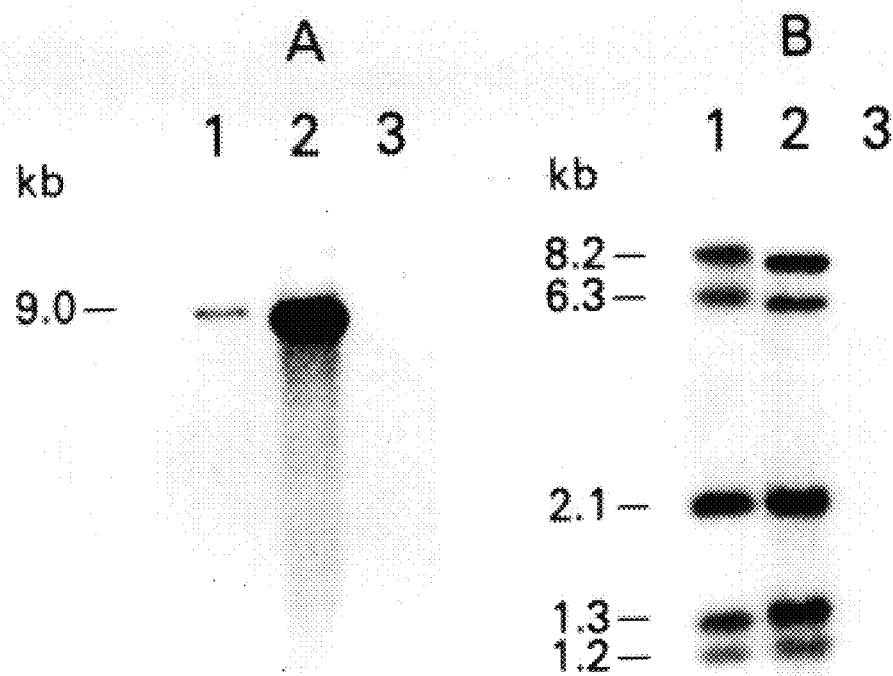
FIGS. 5A and B are Southern blot analyses of HBLV genomic DNA, lanes 1 and 2 are positive for HBLV and lane 3 is negative.
FIG. 5B: EcoRI digested HBLV genomic DNA.

Southern blot analysis of HBLV genomic DNA. Supernatant fluid from HBLV infected umbilical cord blood cells was layered onto 20% glycerol cushions and pelleted by centrifuging at 25,000 rpm for 3 hr. in a Beckman SW41 rotor at 4° C. The pellets were suspended in TNE buffer (10 mM, Tris-HCl, pH 9; 100 mM, NaCl; 1 mM EDTA), and extracted with PCI9 (Phenol:Chloroform:Isoamyl alcohol; 50 mM Tris-HCl, pH9; 100:100:1:10 :: v:v:v:v) followed by Chloroform:isoamyl alcohol (24:1::v:v). Substantially enriched viral DNA was precipitated by adding 2 volumes of 95% ethanol. DNA was digested with Hind III and cloned into the Bluescribe vector (commercially available from Vector Cloning Systems, Calif.). Several clones obtained were prepared as radiolabeled probes and screened for specificity of hybridization by Southern blotting to HBLV infected human umbilical cord blood cell DNA and by in situ hybridization to such infected cells. Results of hybridization of HBLV clone pZHV14 to DNA from pelleted virus digested with Hind III and EcoR1 are shown in FIG. 5. Extracellular virus is shown in lane 1, virus infected human umbilical cord blood cells in lane 2 and negative control DNA isolated from the skin of an AIDS patient in lane 3. Clone pZVH14 scored positive in these assays and did not hybridize to uninfected controls. The infected cell DNA shown in lane 2 is isolated in substantially pure form after several rounds of cell free virus transmission in human umbilical cord blood cells.

In addition to the procedures described above, the following specific methods and materials may also be employed.

Figure 3:
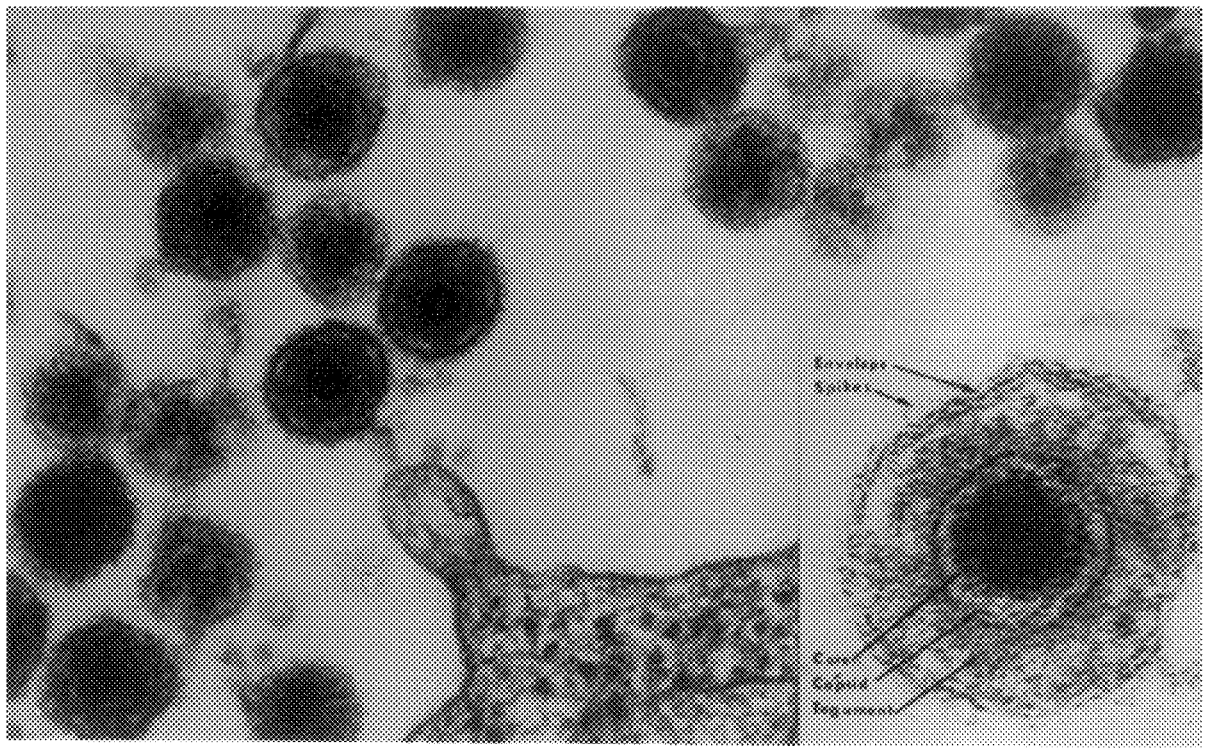
FIG. 3 is an electron micrograph of HBLV showing extracellular enveloped particles, the insert represents a virus particle showing envelope, spikes, core, capsid and tegument.
Figures 4A, 4B, 4C:
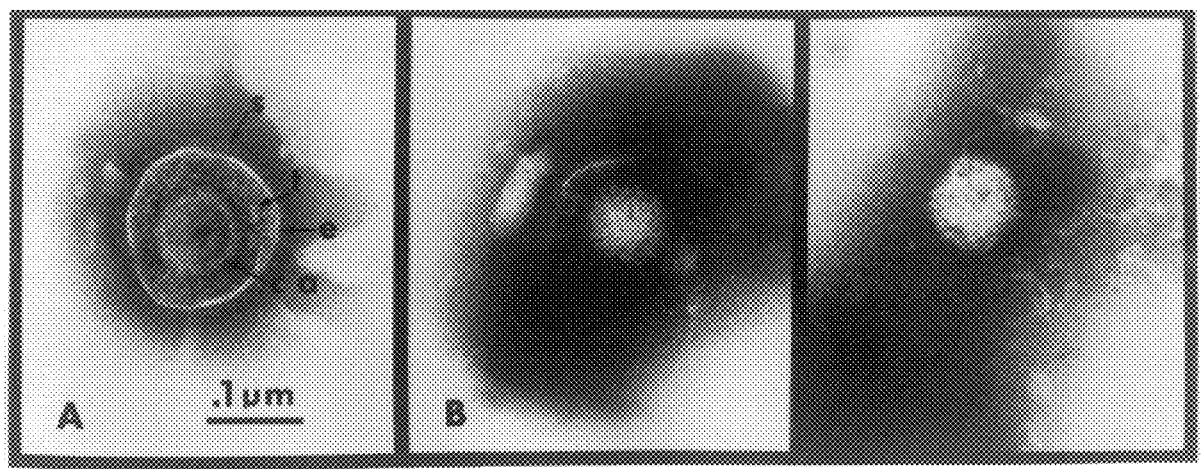
FIGS. 4A, B, and C are an electron micrographs of HBLV (negatively stained).

Rather than using cord blood cells, HBLV can also be propagated by infecting other suitable host cells such as HSB2 cells obtainable from ATCC (CCL 120.1). HBLV(GS) strain was collected from 15 liter cultures of infected HSB2 cells by continuous flow centrifugation onto 10% to 60% sucrose gradients. Bands collected between 1.135 and 1.210 g/ml were pelleted at 20,000 rpm and resuspended in PBS containing 1 mM phenylmethylsulfonyl (PMSF) and 10 mM $MgCl_2$. The suspended virions were subjected to six strokes in a Dounce homogenizer and 23 units per ml of RNAse free DNAse (Boehringer-Mannheim) and incubated for 10 min. at 37° C. The total volume (2ml) was layered onto 36 ml 5–30% dextran T10 gradient (w/w) in 0.5 mM phosphate buffer, pH7, and centrifuged in a Beckman SW 27 rotor for 1 hr. at 20,000 rpm at 4° C. (Dolyniuk et al, J. Virol. 17:935, 1976). Fractions of 4 ml were collected and a visible band was collected in fractions 7–9. Examination of fraction 10 under the electron microscope revealed highly enriched virions with very little cellular debris. Electron microscope examination of virions filtered through 0.2% polyvinylpyrollidone (PVP) treated 0.45 um Nalgene filters also gave excellent results and protein gel analyses showed a purification indistinguishable from fractions 7–9 above by electron microscopy (FIG. 3).

Purification of HBLV genomic DNA

Infection and banding of the virions by continuous flow centrifugation was as described herein supra. The sucrose-banded virus was pelleted at 20,000 rpm in a Beckman SW27 rotor for 90 min. The virus was resuspended in 400 ul of TE buffer (20 mM, Tris-HCl, 1 mM EDTA) and 130 ul of 10% sodium lauryl sarkosinate added. The viral lysate was incubated at 60° C. for 20 min. and then layered onto a 54% CsCl, 0.1 mg/ml ethidium bromide solution and centrifuged in a Beckman SW50 at 45,000 rpm for 20 hr. at 20° C. The viral DNA band (⅓ from the top of the gradient) was visualized under UV illumination and removed by side puncture with a needle and syringe. The HBLV DNA-CsCl aliquot was extracted 5 times with equal volume of n-butanol and then dialyzed against 2 changes of 1000 ml of TE buffer at 4° C. Dialysis membrane was placed over an Eppendorf tube and held in place with an Eppendorf cap into which a hole had been bored. The tube was inverted and floated on the buffer for dialysis. DNA prepared in this way was substantially pure to visualize the ethidium-stained restriction digests on agarose gels and for the creation of plasmid vector libraries. The DNA yield is usually greater than 30 ug per 25 liters of cell free supernatant depending on the extent of the infection.

Labeling of cells

Media for 24 hr. labeling incubations was prepared by mixing 8 ml of methionine free DMEM (D-Met) (Gibco), 2 ml of 50% fetal calf serum in RPMI 1640 and 0.1 ml gentamicin (100×concentrated, 5 mg/ml). Media for 2–3 hr. labeling incubations contained D-Met and 10% fetal calf serum. The amount of 5 mCi of [$^{35}$S]methionine (or other radiolabeled amino acid) was lyophilized and reconstituted with 400 ul of D-Met. Cells in the amount of 5×106 were pelleted at 1000 rpm for 5 min. in the Sorvall GLC bench top centrifuge and resuspended in labeling media. For 24 hr. labeling, the cells were split into two 0.8 ml aliquots in a 24 well microtiter plate and 50 ul of the reconstituted [$^{35}$S] methionine was added to each. For 2–3 hour labeling, 5×10$^6$ cells were resuspended in 1.0 ml of labeling medium and split into two 0.5 ml aliquots and 50 ul of radiolabeled methionine added to each. Cells were incubated at 37° C. under 5% $CO_2$ and 85% humidity for the period of time necessary for labeling.

Radioimmunoprecipitation

After metabolic labeling, (as described herein supra) the cells were diluted in 10 ml of ice-cold phosphate buffered saline (PBS) and pelleted for 5 min. at 1000 rpm in the Sorvall GLC bench top centrifuge, resuspended in 10 ml of fresh ice-cold PBS and pelleted a second time. The cells were resuspended in 1 ml of PBS and transferred to an Eppendorf tube and centrifuged at half maximal speed for 2 min. About 550 ul of lysis buffer [0.1% SDS (sodium dodecyl sulfate), 1% TRITON, X-100, (T-octylphenoxypolyethoxyethanol, Sigma Chemical Company, St. Louis, Mo.) 1% desoxycholate (free acid), 20 mM Tris-HCl, pH 8.0, 150 mM NaCl and 1 mM phenylmethylsulfonyl fluoride (PMSF, Sigma)] was added. The lysate was vortexed at a setting of 5 for 15 sec., allowed to sit on ice for 10 min. and vortexed again. The samples were then centrifuged at top speed in an Eppendorf centrifuge for 3 min. A 50 ul stock aliquot was removed from each tube and immediately frozen on dry ice. The remaining supernatant was transferred to a clean Eppendorf tube and 20 ul of sera was added. The tubes were placed on a rotor at 4° C. and gently inverted for 12 hr. The samples were then centrifuged at top speed for 2 min. and all but 10 ul of the supernatant was removed to a new Eppendorf tube. The amount of 100 ul of a 50% (v/v) slurry of protein A SEPHAROSE, beaded agarose (Pharmacia) in lysis buffer was added to each tube and the tubes gently inverted for 30 min. The samples were centrifuged for 2 min. at top speed and the supernatants discarded. The protein A pellet was washed 6 times by resuspension in lysis buffer and centrifuged for 15 sec. at top speed. After removal of the supernatant of the sixth wash, the pellet was frozen and sent to Protein Data Bases, Inc. (a commercial analytical service laboratory in Huntington Station, N.Y.) for the gel runs.

All radioimmunoprecipitations were performed using serum from patient GS, the source of the prototype HHV-6 isolate. Specificity of the antisera was demonstrated by adsorbing the sera against virion preparations of human cytomegalovirus, Epstein-Barr virus, Varicella Zoster virus, and Herpes Simplex type 1.

High resolution 2 dimensional gels (HR2D) of HHV-6 Proteins

The viral proteins were prepared by SDS-BME (sodium dedecyl sulfate-basic maintenance emulsion) lysis of gradientbanded virions and RNA-DNAse treatment as described herein supra and then frozen on dry ice according to the standard protocols of Protein Data Bases Incorporated (PDI), Huntington Station, N.Y. The samples were run at PDI on 12.5% broad range non-equilibrium and equilibrium polyacrylamide gels and silverstained. The protein-A Sepharose bound radiolabeled immunoprecipitates run on 12.5% broad range non-equilibrium polyacrylamide gels were then exposed for autoradiography at PDI.

It should be noted that in addition to radioimmunoprecipitation (RIP), Western blot, indirect immunofluorescence assay (IFA) enzyme linked immunosorbent assay (ELISA), and the like can also be utilized to detect viral antigens or antibodies. These techniques are well established and known to one of ordinary skill in the art to which this invention belongs.

HR2D Western blotting

Immunoblotting was performed after HR2D electrophoretic resolution of fractions of HBLV prepared from sucrose gradients or filtered virus as described herein supra. The nitrocellulose sheets were stored at 20° C. prior to use. Sheets were incubated for one hour in a blot solution of 4% normal goat serum, 4% fetal bovine serum, 5% non-fat dry milk and 0.02% thimerosal for blocking. Sheets were then incubated with serum from a known HBLV infected patient, diluted 1:1000 in the blot solution. After 3 successive 5 minute washes with PBS, they were reacted in sequence for 1 hour with 1:500 dilution of affinity purified goat anti-human IgG labeled with biotin and for one hour with 1:1000 of horseradish peroxidase streptavidin (Kirkegaard and Perry Labs., Inc., Gaithersburg, Md.) at room temperature (about 21°–25 C.) in 5% normal goat serum in PBS and 0.02% Thimersol. A stock solution of 4-chloronaphthol (4CN stock) was prepared by dissolving 0.3 g of 4-chloronaphthol in 100 ml of methanol. Staining was carried out in a solution containing 2 ml of 4CN stock, 8 ml of PBS and 4 microliters of hydrogen peroxide. The reaction was stopped by washing with distilled water.

Figure 12:
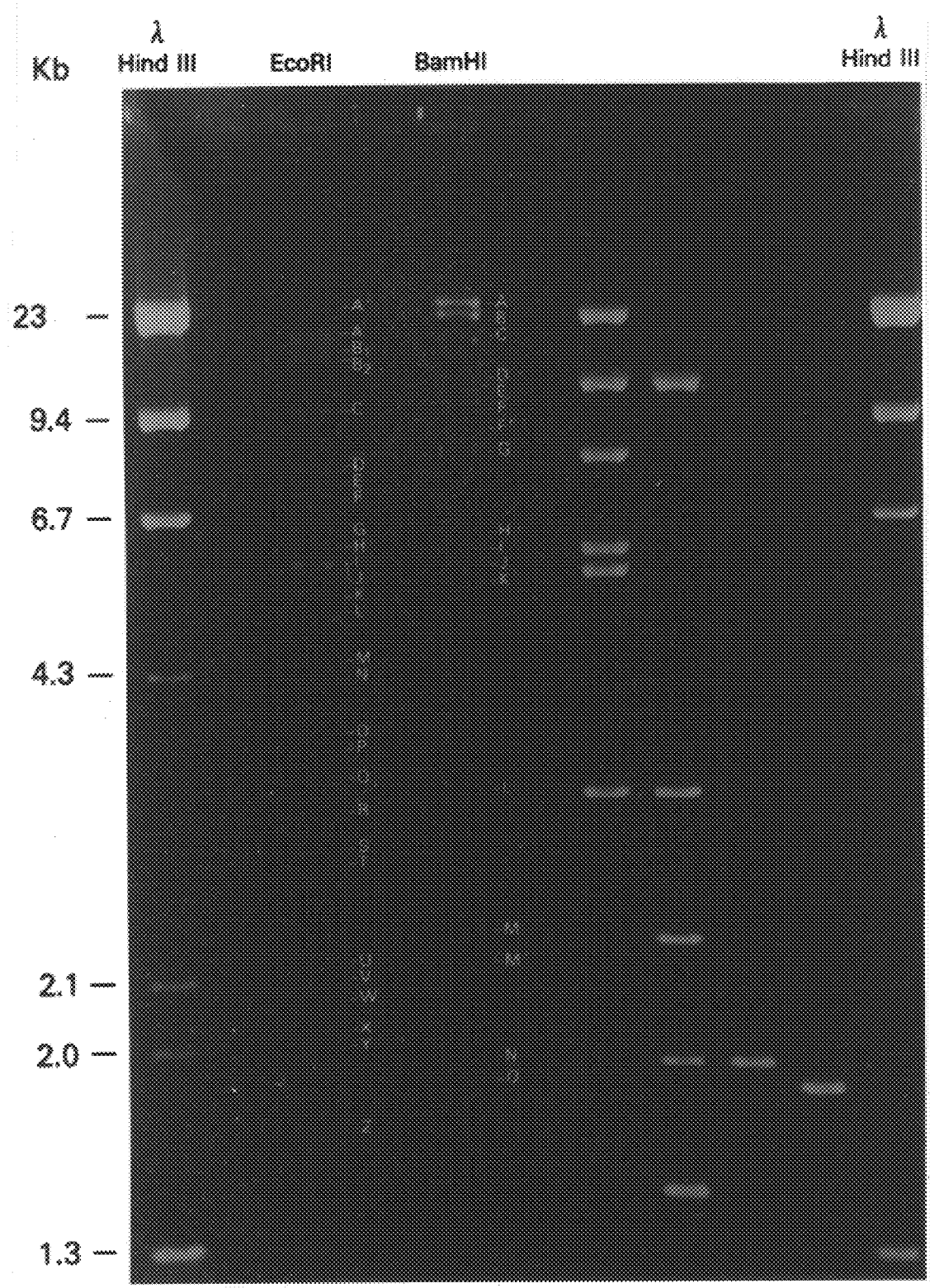
FIG. 12 shows restriction enzyme bands generated using Eco R1 and BamH1 as visualized on a 0.8% agarose gel using ethidium bromide staining.

In order to obtain a better size estimate, DNA was purified from virus collected by continuous flow centrifugation from 15 liters of HBLV infected HSB2 cell culture supernatant and pooled. The regions of the 10% to 60% sucrose gradient pooled were from 1.14 to 1.17 g/ml, fraction A, and from 1.17 to 1.21, fraction B. The virions were pelleted, lysed and the DNA purified by banding on cesium chloride gradients and dialyzed. FIG. 12 shows the restriction enzyme bands generated using EcoRI and BamHI as visualized on 0.8% agarose gels by ethidium bromide staining. Over 26 bands were generated by EcoRI digestion (A to Z, top to bottom) and at least 15 fragments with BamHI (A to O). The bands seen were of similar intensity with a marked absence of submolar fragments. compared to other herpesviruses. Possible exceptions were the EcoRI A' and the BamHI F' and M' fragments which had intensities equivalent to ¼ M. The reasons for the generation of these bands are not understood; however, they are possibly due to genomic inversions and were not counted for the genome size estimates. Table 5 shows the results of restriction enzyme analyses of HBLV.

The construction of BamHI plasmid libraries from the DNA showed that nearly 100% of the fragments cloned were HBLV thereby providing further evidence that the bands visualized in FIG. 12 can be used as a reliable estimate of the HBLV genome size. The molecular weights of the fragments listed in Table 5 gave genome size estimates of 168,000 and 172,000 for the EcoRI and BamHI digests, respectively. By this estimate, the genome of HBLV is approximately the size of the Epstein-Barr virus genome.

Figure 13:
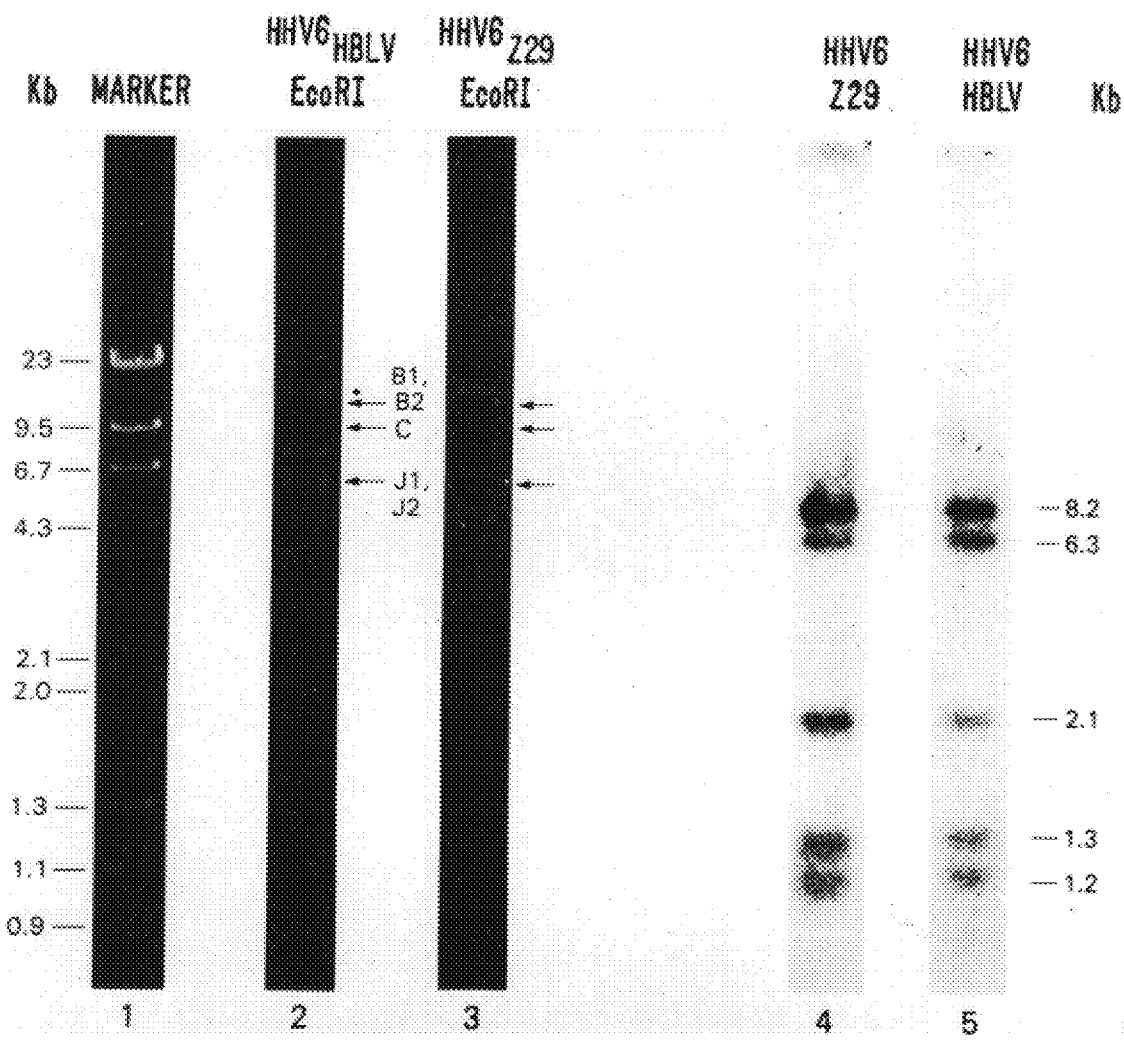
FIGS. 13A and B show restriction endonuclease comparison of a HBLV isolate (HBLV Z29) obtained from the Center for Disease Control and the prototype isolate HBLV (GS). Arrows show the restriction enzyme differences in the EcoR1 restriction patterns between the two isolates.
FIG. 13B: Hybridization of HHV6Z29 and HHV6 HBLV to HBLV probe pzVH14.

Restriction endonuclease comparison of another independent HBLV isolate, HBLV(Z29), to the prototype HBLV (GS) strain is shown in FIG. 13. The arrows indicate the areas where the EcoRI digests of each stain differ as visualized by ethidium bromide staining. Hybridization to one HBLV probe, ZVH14, revealed identical restriction patterns between the two isolates; however, by probe ZVB70, the HBLV(GS) BamHI B fragment, showed differences (not shown). This indicates that restriction site heterogeneity can be observed among different isolates of HHV-6 . Another isolate, HBLV(DV), was identical by hybridization with both the ZVH14 and ZVB70 probes to HBLV (GS).

Studies of the complexity of the enveloped HHV-6 proteins were attempted by banding the virus collected by continuous flow centrifugation on DEXTRAN T-10 gradients similar to methods used to purify the proteins of the enveloped EBV (Dolyniuk et al, 1976, supra). The virions obtained from continuous flow centrifugation were pelleted, treated with DNAse 1 and then banded on 10% to 30% DEXTRAN T-10 gradients. The various fractions collected from the top were analyzed by electron microscopy and the virus was pelleted from those which looked relatively free of cellular debris. A viral band was seen toward the bottom of the gradient (fractions 7–9) and the fraction immediately below (fraction 10) was considered to be relatively free of cellular debris when compared to virus obtained after a single banding. The virus was found in clusters with little cellular material. Virus prepared by this method when inoculated into rabbits resulted in the generation of HBLV specific antibodies in 14 days which were readily detected by indirect immunofluorescence assay on infected cells. Subsequent bleeds gave some non-specific cellular background in IFA tests. Hence, the animals should be bled about 14 days post inoculum. These antibodies can be utilized for detection of HBLV by established techniques.

Figure 6:
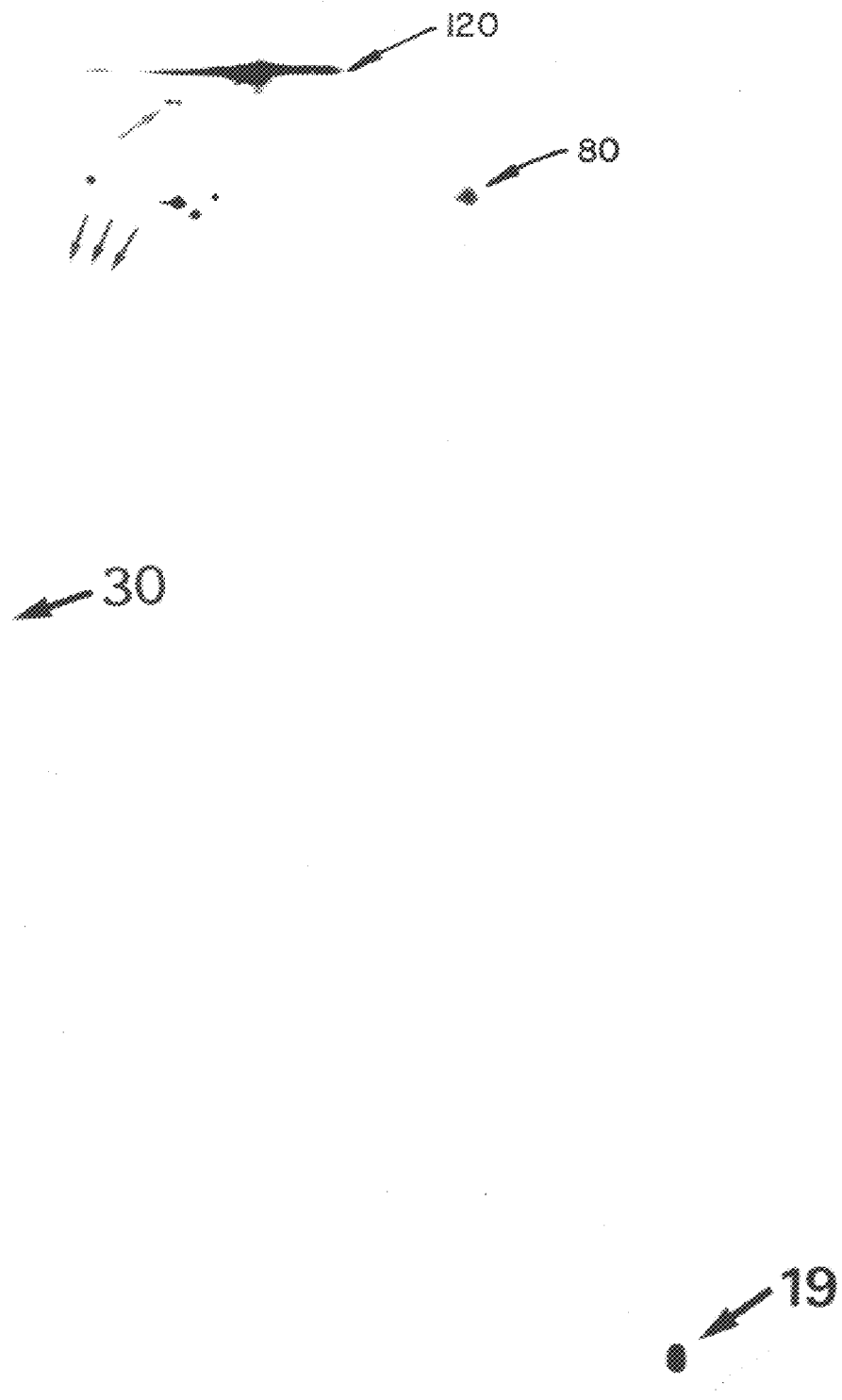
FIG. 6 shows HBLV proteins after radioimmunoprecipitation using a positive patient (GS) serum and two dimensional (2D) gel electrophoresis. HBLV specific proteins are indicated by arrows according to apparent molecular size in KDa.
Figures 9A, 9B:
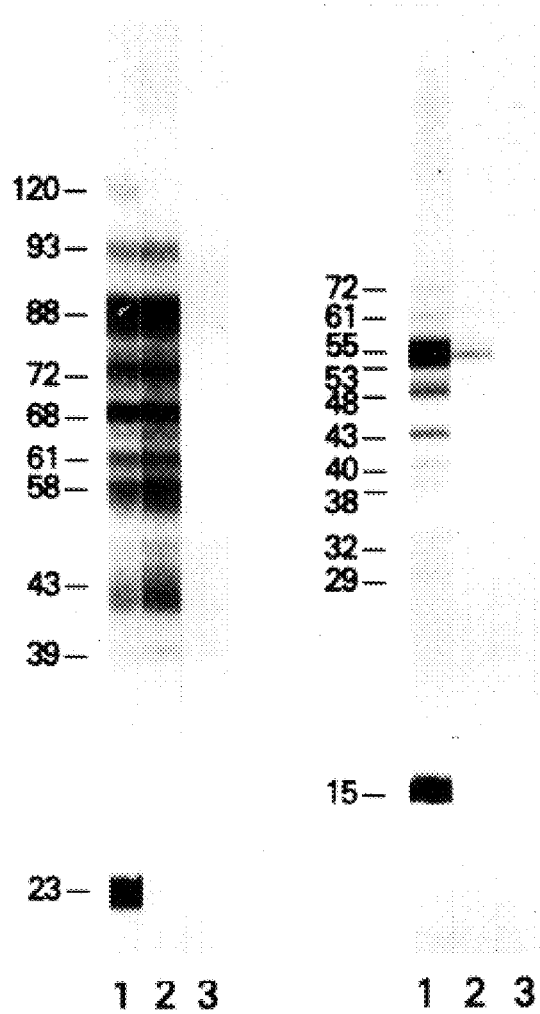
FIGS. 9A and B show Western blot analyses of HBLV proteins.
FIG. 9B: HSB 2-Cell Lysates.
Figure 10:
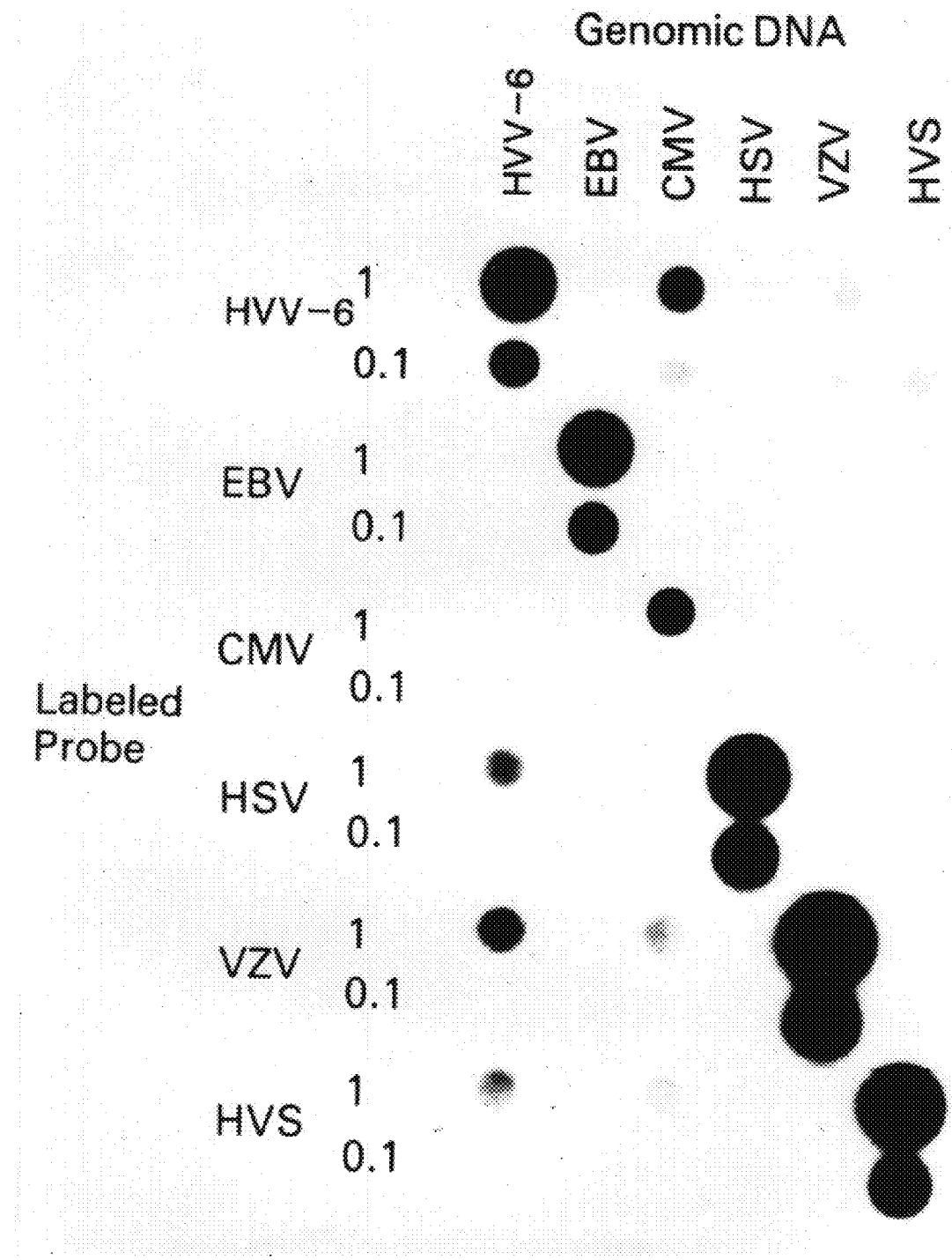
FIG. 10 shows dot blot analysis of various herpesviruses, showing specificity for the probes to their genomic DNA.
Figure 11A:
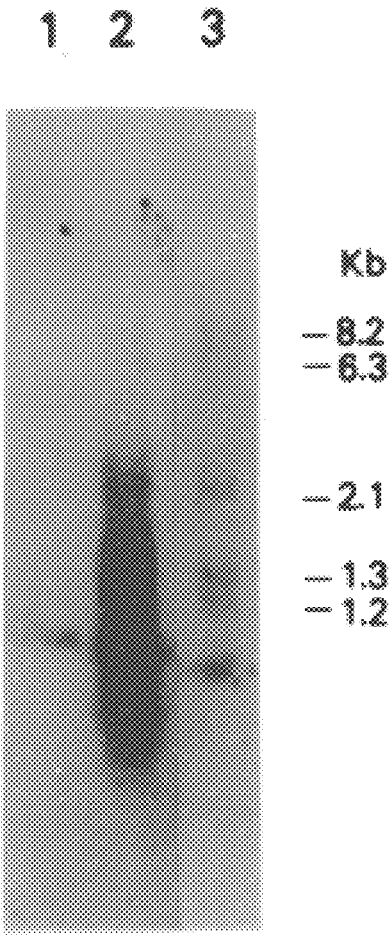
FIGS. 11A, B and C show Southern blot using pZVH14 probe for detecting HBLV in three human B-cell tumors.
Figure 11B:
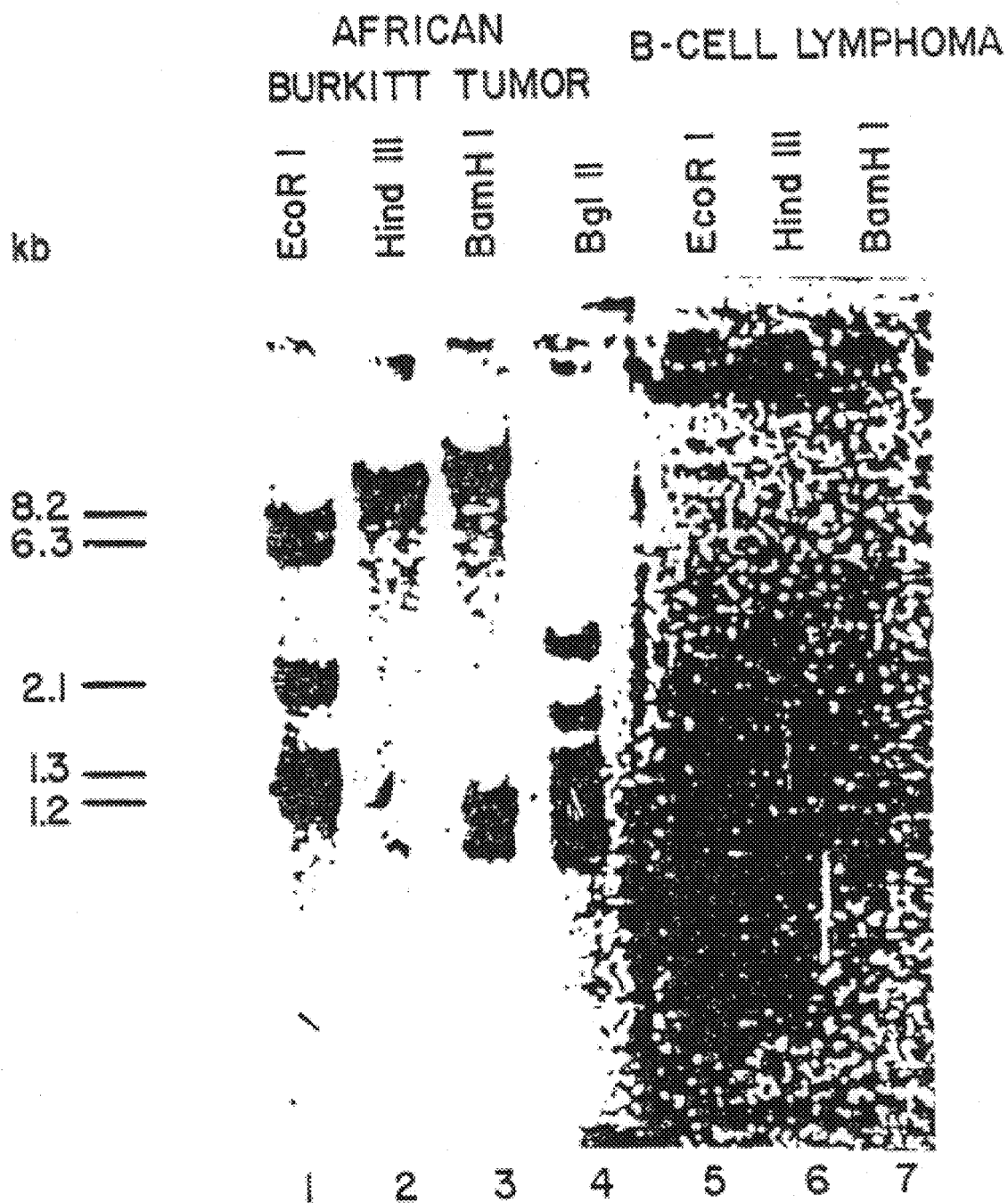
FIG. 11B: Detection of HBLV sequences in an African Burkitt tumor.
Figure 11C:
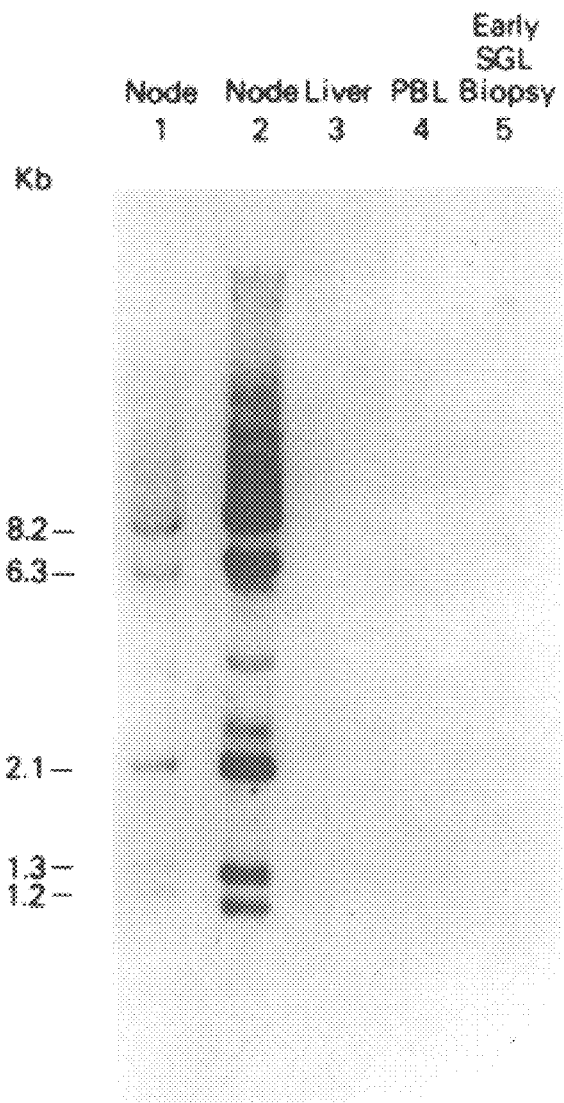
FIG. 11C: Detection of HBLV sequences in Multicentric Tumors arising in a Sjogren's Syndrome patient.
Figure 14:
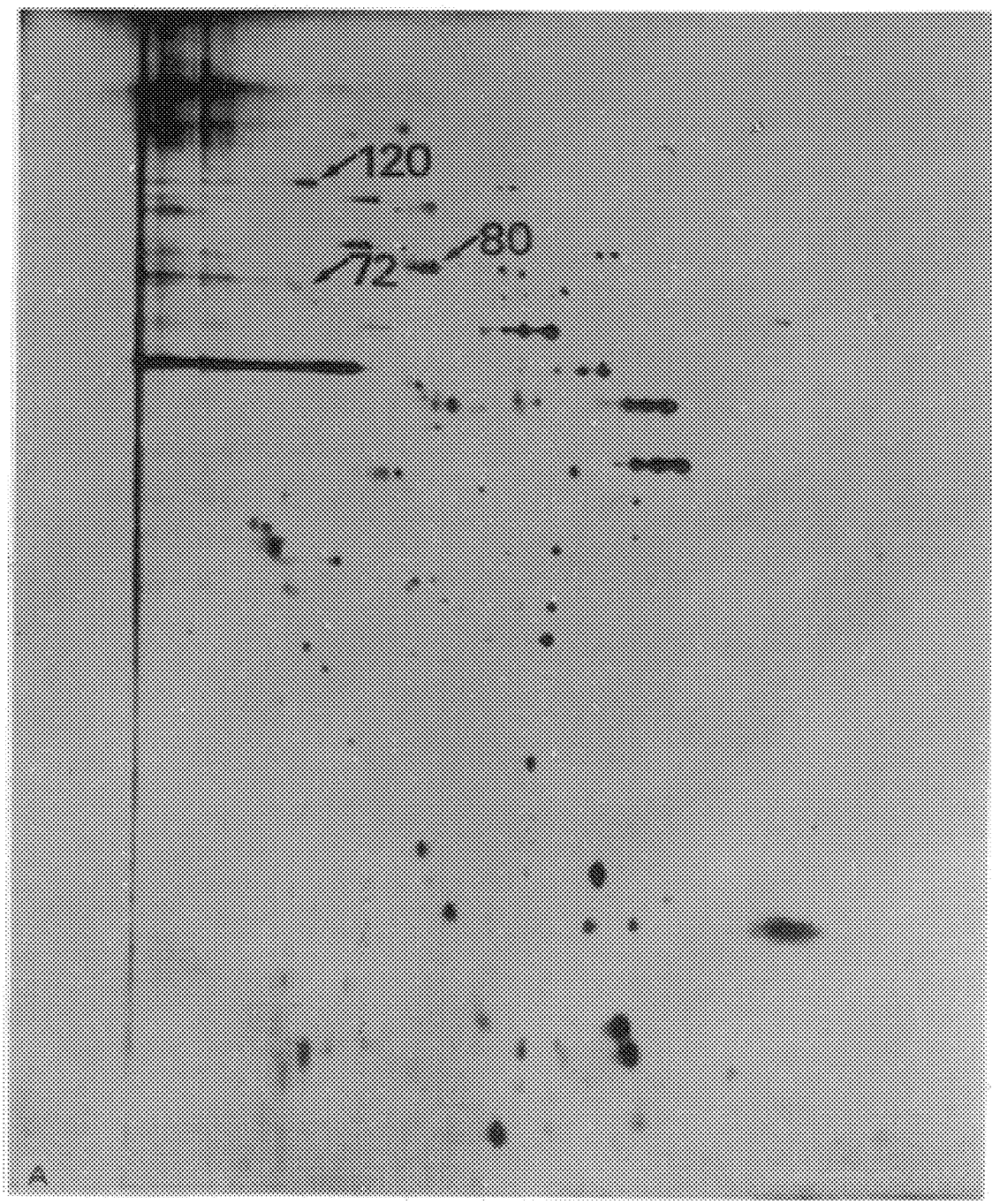
FIG. 14 shows the silver stained gel with enriched HBLV proteins.
Figure 15:
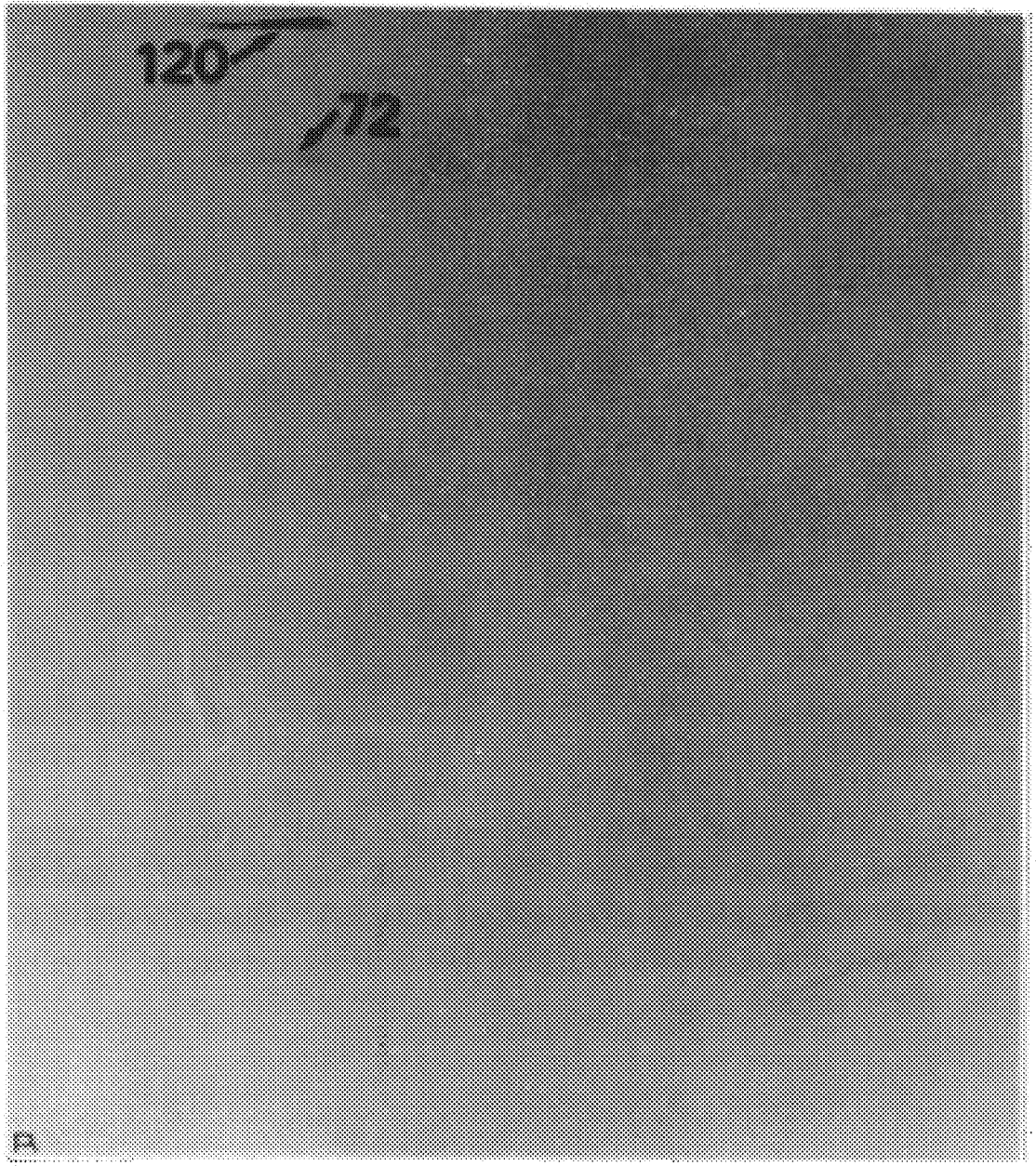
FIG. 15 is a Western blot of the gel run in parallel with gel of FIG. 14. Clearly 120 and 72 KDa proteins are detected.
Figure 17:
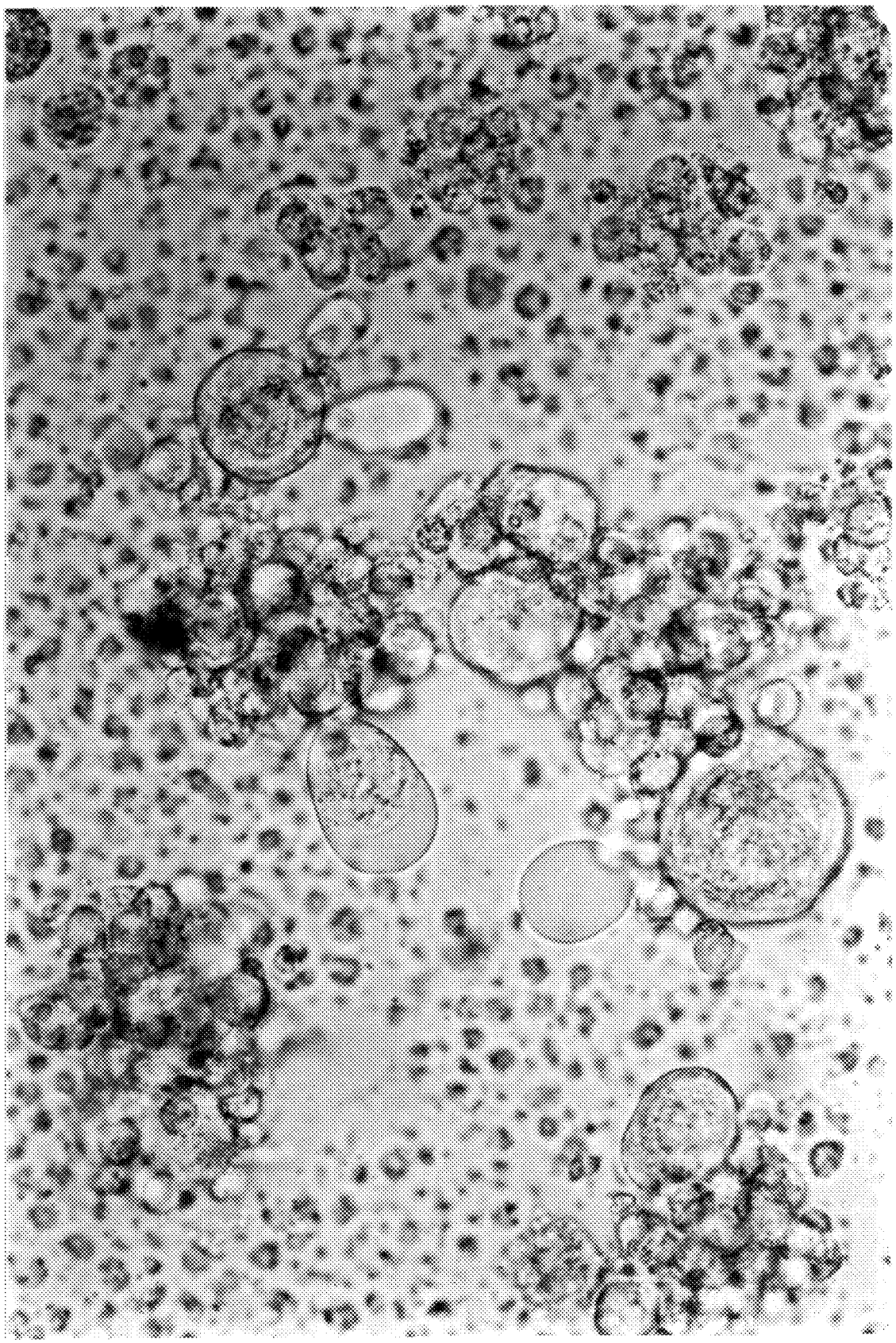
FIG. 17 shows HBLV infected human umbilical cord blood lymphocytes. Large refractile infected cells are prominent.

The pure preparations of the virus as revealed by electron micrographs, were used to determine the proteins by direct visualization on high resolution two dimensional polyacrylamide gels (HR2D). As mentioned herein supra by procedures developed at Protein Data Bases, Inc., several 12.5% broad range non-equilibrium gels were run and a gel of the virions obtained from the DEXTRAN T-10 fraction 10 was silverstained (FIG. 14). A parallel gel was run and Western blotted using GS serum and peroxidase conjugated goat anti-human antibody. Two major proteins were detected at 120 and 72 kDa as shown in FIG. 15. Radioimmunoprecipitation of HBLV-infected cell lysates with the GS serum showed several additional proteins (FIG. 6). In addition to the proteins detected by Western blots, radioimmunoprecipitations performed on proteins from lysates of metabolically labeled cells showed a protein at 120 kDa; however, additional major proteins at 200, 80 and 19 kDa, as well as some minor proteins at 60 kDa, 80 kDa and several in the 30 kDa range were also detected. Two forms of the 19 kDa proteins were observed, a more acidic form, 19a, and a more basic major form, 19b, possibly due to differences in phosphorylation (FIG. 6). The antigenic proteins can then be isolated in substantially pure form following standard purification techniques, such as column chromatography, HPLC, preparative gel electrophoresis, and the like. These proteins can be identified, for example by Western blot using HBLV antibody positive sera. A pharmaceutical composition in accordance with the present invention comprises an immunogenic amount of the antigenic protein in a pharmaceutically acceptable carrier. Antigenic proteins or portions thereof can also be obtained from gt11 expression libraries or the like.

Antigenic proteins of the present invention also allow detection of the presence of HBLV antibodies in a biological sample by reacting said sample with the viral antigens, a positive antigen-antibody complex formation being indicative of HBLV infection. Antigen-antibody reactions can be detected by any standard immunological techniques well known to one of ordinary skill in the art, such as radioimmunoassay, Western blot, ELISA, immunofluorescence, histoimmunological tests and the like.

EXAMPLES

Example 1. Fresh tissue sections from 3 patients were found to contain a low number of HBLV-infected cells. One patient, a 40 year old Hispanic with a history of IV drug use, was seropositive for both HTLV-I and HTLV-III, and was diagnosed with AIDS-pneumocystic pneumonia with associated dermatopathic lymphadenopathy. Another was a 61 year old white male who received multiple blood transfusions in conjunction with open heart surgery 4 years prior to death. This patient was seropositive for HTLV-III and was diagnosed with immunoblastic lymphadenopathy with some skin involvement. A third patient (GS) was a 16 year old black male diagnosed with acute lymphocytic leukemia of the T-cell type. Unlike the others, this patient was seronegative for HTLV-III. Primary peripheral blood mononuclear cell cultures from these patients also contained a small number of the unique cells which, upon close examination, were also found to be infected by HBLV.

Example 2. A direct comparison of molecularly cloned sequences of the HBLV genome with the genomes of other herpesviruses was also conducted. Several DNA clones obtained from nucleic acids extracted from purified virus were examined for specificity and for comparison with other DNA viruses. Two HBLV clones, designated pZVH14 (FIG.

8) and pZVB70 (FIG. 16 ATCC No. 40473), were used in these studies. Southern blot analysis (FIG. 5) showed the presence of viral specific DNA in Hind-III and EcoRI digests of DNA from both purified virus and HBLV-infected human cord blood cells. In situ hybridization experiments with the pZVH14 probe also confirmed that these sequences were confined to the infected cells (FIG. 1).

Example 3. Monoclonal antibodies and hyperimmune sera prepared against human and simian herpesviruses were tested for reactivity with HBLV infected cells by indirect immunofluorescence procedures as described herein above. Monoclonal antibodies to EBV and HCMV were used at 1:40 dilution; HSV-I and II, VZV and HVS at a 1:10 dilution and normal ascites fluid was used at 1:5 and 1:10 dilutions. Hyperimmune sera to African green and Rhesus monkey CMV were heat inactivated (50° C. 30 min.), clarified at 10,000 rpm, and then were used at 1:10 dilutions. In addition to the sera shown, human sera containing antibodies to EBV, CMV, HSV-I and II, and VZV also did not react with HBLV infected cells. African green monkey and Rhesus sera containing antibody to CMV were also negative when tested with HBLV. Monoclonal antibodies to EBV and HCMV, and ascites fluid from normal mouse were gifts from Dr. Gary Pearson, School of Medicine, Georgetown University, Washington, D.C. Monoclonal antibodies to VZV and HVS were obtained from Dr. Nancy Chang, Baylor College of Medicine, Houston, Tex., and Dr. John Dahlberg, NCI, Bethesda, Md., respectively. HSV-I and II monoclonal antibodies were purchased from Dupont, Boston, Mass. Hyperimmune serum to purified African green and Rhesus CMV were previously prepared in rabbits by Dr. Ablashi. The specificity of the serum containing antibodies to HBLV was shown by adsorbing it against the other human herpesviruses (either whole virus or infected cells).

Abbreviations used: HBLV, Human B lymphotropic virus; EBV, Epstein-Barr virus; HCMV, Human cytomegalovirus; HSV, Herpes simplex virus; VZV, Varicella-Zoster virus: HVS, Herpes virus saimiri, VCA (Viral capsid antigen); EA, early antigen; MA, membrane antigen.

HBLV infected cord blood mononuclear cells were stained with an HBLV negative serum resulting in a considerable number of large cells with no immunofluorescence.

Example 4. Serum from Old World and New World primates were tested for antibody to HBLV by indirect immunofluorescence as described.

Some sera from the Old World primates were gifts from Dr. P. Kanki, Harvard School of Public Health, Boston, Mass. All sera were heat inactivated at 50° C. for 30 minutes, and clarified by centrifugation before use. HBLV-infected cord blood leukocytes, P3HR-1 (an established cell line expressing EBV-VCA), and Owl monkey kidney cells infected by HSV-strain II were used for comparisons. When infected cells showed cytopathic effects, the cells were fixed in acetone and used for the IFA test.

Three owl monkeys and one cottontop marmoset were previously inoculated with HVS. Sera from these Animals possessed antibody to HVS late antigen which cross-reacted with Herpesvirus ateles. The results are presented in Table 2.

Example 5. In situ hybridization of HBLV-infected human cord blood cells. Tests were performed utilizing $^{35}$S-labeled RNA probes as described herein supra. Clone pZVH14 of the HBLV genome was used as a template for radiolabeled RNA using T7 RNA polymerase, $^{35}$S-labeled GTP, and unlabeled ribotriphosphates. Less than one grain per cell was observed in uninfected negative control cultures. Large refractile cells characteristic of the infected cultures were heavily labeled, indicating the expression of abundant viral messages (FIG. 1).

Example 6. Two dimensional gel electrophoresis patterns of proteins recognized by human sera against human B cell lymphotropic virus (HBLV) are shown in FIG. 6. Human umbilical cord blood lymphocytes or $HSB_2$ cells were infected with HBLV and then labeled by incubation with $^{35}$S-methionine for periods of either 3 hours or 24 hours. H9 cells were used as negative controls. The labeled cells were lysed and the proteins immunoprecipitated according to established procedures (Protein Data Bases, Inc., New York). Spotsseen on the gels of the lysates from infected cells but not seen on the control gels represent candidate virus proteins arrayed in unique virus specific patterns. These patterns serve as a fingerprint which can specifically identify HBLV. The proteins detected are antigenic proteins, the coding sequence of which can be cloned and expressed, and the purified proteins thus obtained can be used as diagnostic reagents.

PREPARATION OF THE CLONES

Of course, the availability of the biologically pure HBLV and its DNA, allows the preparation of the clones of HBLV. A general method of cloning the Human B Lymphotropic Virus (HBLV) genome involves isolating viral DNA after infection of suitable host cells (such as $HSB_2$ and the like), primary cells or cord blood cells with the HBLV virus. The unintegrated viral DNA is then cloned in a suitable cloning vector such as a plasmid or a lambda phage to create libraries which can be screened for the presence of viral specific DNA fragments.

Infected cells and cultured peripheral cord blood cells produce HBLV virus and serve as the principal source of the virus for immunological assays and the like for detecting virus-specific antigens and antibodies in human sera. Cultures of infected cells are grown and the virus harvested from the supernatant and the high molecular weight DNA extracted from the virus. This produces viral DNA containing the HBLV genome of the present invention. This DNA is then subcloned in a suitable plasmid to produce a clone. A complete description of the procedures for preparing clones can be found in such standard publications as Maniatis et al: "Molecular Cloning," Cold Spring Harbor, N.Y.

Two elements of the above process are well known are a part of the recombinant DNA procedures: the DNA library and the differential screening of DNA inserts to infected and uninfected cells. The library is formed by taking the total DNA from the enriched or purified virus DNA, cutting the DNA into fragments with suitable restriction enzyme(s), joining the fragments to plasmid vectors, and then introducing the recombinant DNA into a suitable host. The viral specific DNA fragments are distinguished by their hybridization to infected cell DNA and/or by in situ hybridization to infected cells but not to uninfected cells.

As shown herein infra, a molecular clone, pZVH14, of the HBLV genome is useful as a template for radiolabeled RNA using T7 RNA polymerase, $^{35}$S-labeled GTP, and unlabeled ribotriphosphates.

In the preferred embodiment of the present invention, supernatant fluid from HBLV infected cells is layered onto 20% glycerol cushions and pelleted by centrifuging at 25,000 rpm for 3 hr. in a Beckman SW41 rotor at 4° C. The pellets are suspended in TNE buffer (10 mM, Tris-HCl, pH 9; 100 mM, NaCl; 1 mM EDTA), and extracted with PCI9 (Phenol:Chloroform:Isoamyl alcohol; 50 mM Tris-HCl, pH9; 100:100:1:10 v:v:v:v) followed by chloroform;isoamyl alcohol (24:1::v:v). Enriched viral DNA is precipitated by adding 2 volumes of 95% ethanol. DNA is digested with Hind-III and cloned into the Bluescribe vector (commercially available from Vector Cloning Systems, Calif.). Several clones obtained after screening with labeled, enriched, DNA were examined for specificity of hybridization to the HBLV DNA and by in situ hybridization to HBLV-infected cells.

Clones pZVH14 and pZVB70 which were thus produced, scored positive when tested by hybridization techniques and did not hybridize to uninfected controls. The infected cell DNA is isolated after several rounds of cell free virus transmission in human umbilical cord blood cells or $HSB_2$ cells. Clone pZVB70 was obtained from CsCl gradient banded DNA of sucrose banded virus. DNA was BamH1 digested as described herein supra.

It is noted that these probes, either alone or in combination, can be employed for detecting the viral DNA or RNA and virus-infected cells containing HBLV nucleic acids by any of several standard techniques well known to one of ordinary skill in the art. Examples of such well established techniques are Southern and dotblot for DNA analysis, Northern blot for RNA analysis and in situ hybridization. Furthermore, a probe for in situ hybridization can be made by any of well established procedures such as radio-labeling or covalent linkage of hapten or enzyme to DNA. A few illustrative examples are now provided.

Example 7. Several DNA clones obtained from nucleic acids extracted from purified virus obtained as described above, were examined for specificity relative to other DNA viruses. HBLV clone designated pZVH14, contained a 9.0 kb Hind III fragment. Southern blot analysis showed the presence of viral specific DNA in Hind-III and EcoRI digests of DNA from both purified virus and HBLV-infected human cord blood cells. In situ hybridization tests with the same probe also confirmed that these sequences were confined to infected cells.

Figures 8, 16:
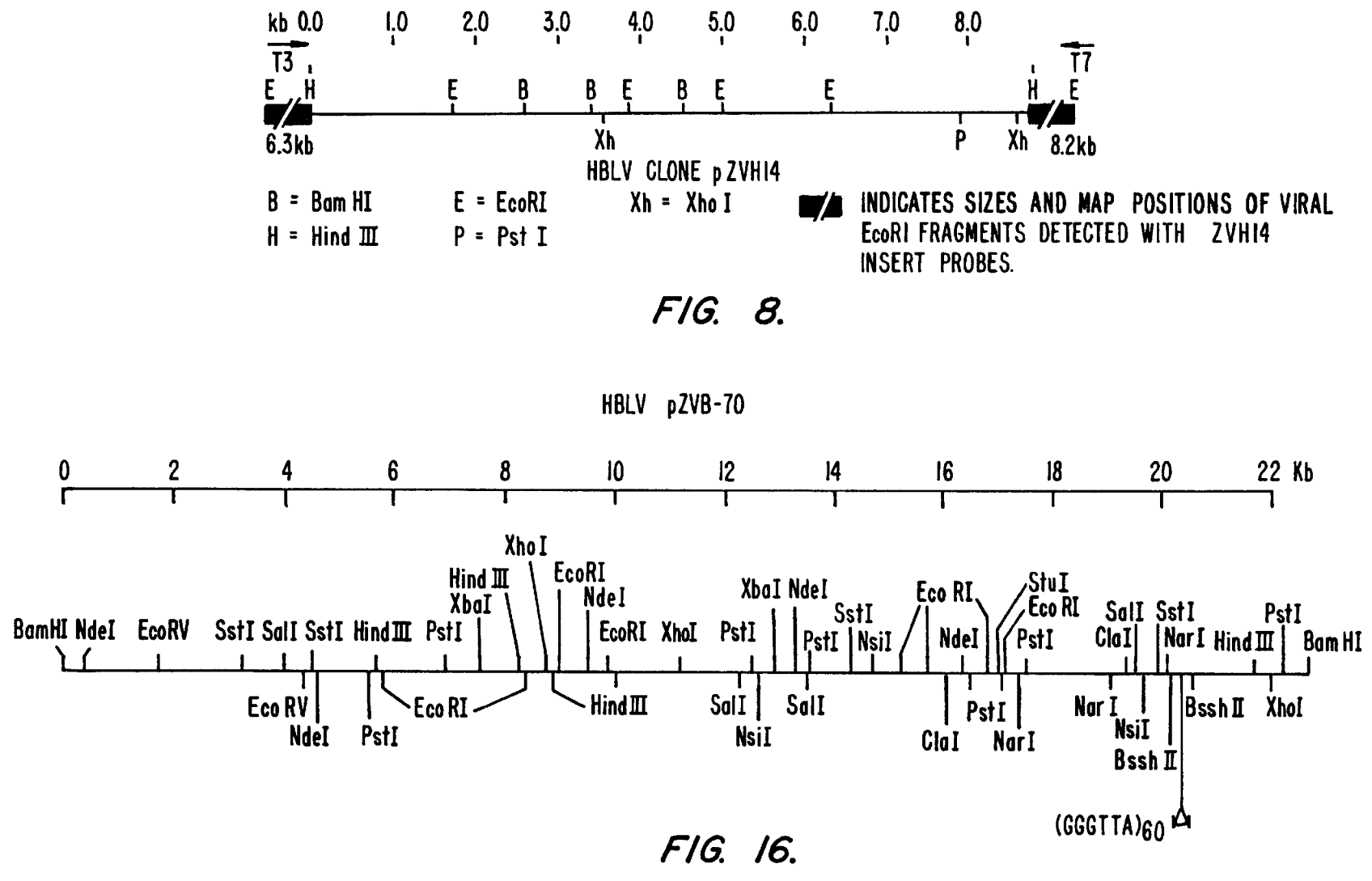

Example 8. Human B Lymphotropic Virus clone pZVH14 has been restriction enzyme mapped as shown in FIG. 8.

Example 9. Similarly, HBLV clone pZVB70 has been restriction enzyme mapped as shown in FIG. 16.

It is noted that based on the sequence information, any number of specific clones can be generated and used as probes. The techniques are well established and known to one of ordinary skill in the art to which this invention belongs.

Example 10. In situ hybridization of HBLV-infected cells. Tests were conducted utilizing $^{35}$S-labeled RNA probes as described herein supra. Clone pZVH14 of the HBLV genome were used as a template for radiolabeled RNA using T7 RNA polymerase, $^{35}$S-labeled GTP, and unlabeled ribotriphosphates. Less than one grain per cell was observed in uninfected negative control cultures. Large refractile cells characteristic of the infected cultures were heavily labeled, indicating the expression of abundant viral messages (FIG. 1).

Example 11. Based on the nucleotide sequence, polymerase chain reaction technique (Saiki et al, 1985, BioTechnology, 3:1008; Science, 230:1350) was employed to obtain increased levels of nucleic acids from specimens (tissue or cell culture) suspected of HBLV infection from diseased and normal A (control) populations and the presence of HBLV detected by Southern blotting of the amplified HBLV DNA or other method of detecting the amplified DNA with radiolabeled or nonradiolabeled probes as are well known to one of ordinary skill in the art.

A deposit of the clones pZVH14 and pZVB70 have been made at the ATCC, 10801 University Boulevard, Manassas, Va. 20110-2209 under the accession numbers 40,247 and 40,473, respectively. The deposit shall be viably maintained, replacing if it becomes non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

In summary, as demonstrated herein, high level production of HBLV can now be obtained by the use of the HSB2 or other cell lines. This allows purification of the enveloped virus and the viral nucleic acids. Purification of the viral DNA has been demonstrated by hybridization with specific cloned viral DNA such as clone pZVH14. Although the size estimate (170,000) of the HBLV genome is similar to that of EBV, evidence by molecular hybridization shows distant relationships to the human cytomegalovirus and to the Marek's disease cirrus of chickens (data not shown).

Comparison of the Western blots from the HR2D gels to the radio-immunoprecipitation revealed a major antigenic protein of 120 kDa and other antigenic proteins described herein supra which is detectable by both (RIP and Western blot) methods. The 120 Kd protein seems to be a major antigenic protein as demonstrated by anti-HBLV patient sera. Increased resolution of the minor proteins on 2D gels indicates that it would be easier to verify the presence of characteristic viral proteins by this method than by 1D gels. Very clean background seen in the two dimensional Western blot, in which 120 Kd and 72 Kd proteins were detected, may be the method of choice.

Although not necessary, because biologically pure virus can be obtained by following the standard procedures described herein by anyone of ordinary skill in the art, nevertheless a deposit of the isolated virus has been made at the ATCC, Rockville, Md. under accession number VR2225. A deposit of the anti-HBLV positive serum has also been made at the ATCC under accession number 40476. The deposits shall be viably maintained, replacing if it becomes non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

A diagnostic kit in accordance with the present invention comprises containers separately containing anti-HBLV antibodies, one or more purified or cell associated antigenic viral protein(s) produced by HBLV in any part of its replicative cycle (i.e., HBLV infected cells or cells expressing specific HBLV proteins); HBLV specific nucleic acid probes; positive and negative controls and instructional material to perform diagnostic test employing said antibodies, antigenic viral protein(s), probes and the like. Of course, the present invention also allows the detection of HBLV present in any biological sample. Any suitable method mentioned herein can be utilized as deemed most appropriate by one of ordinary skill in the art, depending on such factors as the location, nature, amount of the sample available and the like.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

ISOLATION OF HBLV FROM PERIPHERAL BLOOD LYMPHOCYTES OF PATIENTS WITH LYMPHOMA AND LYMPHADENOPATHY

| Patient | | Description | Serology* HTLV | HBLV | HBLV Isolation** |
|---|---|---|---|---|---|
| 1 | RC 29 WM | AIDS KS B cell lymmphoma | +III | 1:80 | + |
| 2 | WR 57 WM | OHS AILD | — | 1:40 | + |
| 3 | PD 40 WM | Dermatopathic lymphademopathy; IVDA T8$^+$ skin infiltrate | +II and +III | 1:80 | + |
| 4 | GS 17 BM | T-cell ALL (T-4$^+$) | — | 1:160 | + |
| 5 | RW 66 RM | Mycoses Fungoides (T-4$^+$) Cutaneous T-cell Lymphoma | — | 1:80 | + |
| 6 | BD 35 BF | Immunoblastic Lymphoma | — | 1:80 | + |

*Serology was done by indirect immunofluorescence using as standard a reference virus isolated from patient GS.
**PBL from patients were cultured as the primary source of virus. Virus particles were transmitted to fresh human cord blood. Positive cultures were identified by morphology, IF, and EM.

TABLE 2

Cross-Reactivity of Nonhuman Primate Sera

| | Virus Used to Infected Target Cells | | | | | |
|---|---|---|---|---|---|---|
| No. Positive No. Tested Serum Sources | HBLV No. Positive (VCA)/No. Tested (Percent Positive) | | EBV No. Positive No. Tested (Percent Positive) | | HSV (Percent Positive) | |
| Old World Primates | | | | | | |
| Chimpanzee | 0/5 | (0) | 5/5 | (100%) | 0/4 | (0) |
| Gorilla | 0/3 | (0) | 2/3 | (66.6%) | 0/3 | (0) |
| Orangutan | 0/2 | (0) | 1/2 | (50%) | 0/2 | (0) |
| Baboons | 0/3 | (0) | 3/3 | (100%) | 0/3 | (0) |
| Stumptail | 0/2 | (0) | 1/2 | (50%) | 0/2 | (0) |
| Rhesus | 0/9 | (0) | 6/9 | (66/6%) | 0/7 | (0) |
| African Green | 0/10 | (0) | 6/10 | (60%) | 0/10 | (0) |
| New World Primates | | | | | | |
| Squirrel monkeys | 0/10 | (0) | 0/10 | (0%) | 8/10 | (80) |
| Owl monkeys | 0/6 | (0) | 0/6 | (0%) | 3/6 | (50) |
| Marmosets (common) | 0/6 | (0) | 0/6 | (0) | 0/6 | (0) |
| Marmoset (cottontop) | 0/3 | (0) | 0/3 | (0) | 1/3 | (33.3) |

TABLE 3

Immunological Cross Reactivites of HBLV to Other Human and Nonhuman Primates Herpesviruses Antibody Viruses Used to Infect Target Cells

| Source | HBLV | EbV | PCMV | HSV-I and II | VZV | HVS | Af. Gr. CMV | Rhesus CMV |
|---|---|---|---|---|---|---|---|---|
| ERV Monoclonal Antibody (VCA, EA, MA) | – | + | – | – | – | – | – | – |
| HCMV Monoclonal Antibody | – | – | + | – | – | – | – | – |
| HSV I and II Monoclonal Antibody (early and late antigens) | – | – | – | + | – | – | – | – |
| VZV Monoclonal Antibody (late antigens) | – | – | – | – | + | – | – | – |
| HVS Monoclonal Antibody (late anitgens) | – | – | – | – | – | + | – | – |
| Af. Green Monkey CMV (hyperimmune serum) | – | – | – | – | – | – | + | – |
| Rhesus Monkey CMV (hyperimmune serum) | – | – | – | – | – | – | – | + |

TABLE 4

Morphologic comparison of HBLV with other herpes viruses

| Feature | HBLV | HSV* | HCMV(6) | EBV(7) |
|---|---|---|---|---|
| Diameter of nucleoid | 60–80 nm | 50–70 nm | 64.3 nm | 48 nm |
| Diameter of capsid | 95–105 nm | 95–110 nm | 106.4 nm | 80 nm |
| Symmetry of capsid | Icosahedral | Icosahedral | Icosahedral | Icosahedral |
| No. of capsomeres in capsid | 162 | 162 | 162 | 162 |
| Thickness of tegument | Dense, prominent, 25–40 nm | Often indistinct, 20–40 nm | Dense, prominent, 24.4 nm | Variable, 20 nm |
| Diameter of enveloped virion | 160–200 nm | 150–200 nm | 174 nm | 120 nm |

*HSV used for this comparison was prepared simultaneously and under identical conditions as HBLV.

TABLE 5

| Fragment | MW (kb) |
|---|---|
| EcoR1 | |
| A | 20.0 |
| B | 17.0 |
| C | 16.0 |
| D | 10.5 |
| E | 8.0 |
| F | 7.7 |
| G | 7.4 |
| H | 6.6 |
| I | 6.3 |
| J1,J2 | 5.9 |
| K | 5.4 |
| L | 5.0 |
| M | 4.5 |
| N | 4.36 |
| O | 3.85 |
| P | 3.75 |
| Q | 3.5 |
| R | 3.25 |
| S | 3.05 |
| T | 2.95 |
| U | 2.5 |
| V | 2.4 |
| W | 2.3 |
| X | 2.25 |
| Y | 2.1 |
| Z | 1.75 |
| Z1 | 1.5 |
| Z2 | 1.49 |
| Z3 | 1.35 |
|  | 168.55 |
| BamH1 | |
| A | 40.0 |
| B | 30.0 |
| C | 23.1 |
| D | 13.5 |
| E | 11.8 |
| F | 10.9 |
| G | 8.5 |
| H | 6.5 |
| I | 6.2 |
| J | 5.95 |
| K | 5.6 |
| L | 3.4 |
| M | 2.6 |
| N | 2.05 |
| O | 1.95 |
|  | 172.05 |

What is claimed is:

1. An isolated polypeptide encoded by a first nucleic acid which hybridizes under stringent conditions to a second nucleic acid from an isolated human herpes virus having the morphology of a human herpes virus and a double-stranded DNA genome of about 170 Kb, wherein genomic DNA from said isolated human herpes virus hybridizes under stringent conditions with nucleic acid of molecular clone ZVH14 (ATCC Accession No. 40,247); and further wherein said first nucleic acid does not hybridize under said stringent conditions with the nucleic acid of:

(a) Epstein-Barr virus;
   (b) human cytomegalovirus (CMV);
   (c) Herpes Simplex virus (HSV);
   (d) Varicella-Zoster virus (VZV); or
   (e) Herpes virus saimiri.

2. The polypeptide of claim 1, wherein said polypeptide is specifically bound by antibodies in human serum from a patient infected with the isolated human herpes virus.

3. A composition comprising antigenic protein of an isolated human herpes virus having the morphology of a human herpes virus and a double-stranded DNA genome of about 170 Kb, wherein genomic DNA from said isolated human herpes virus hybridizes under stringent conditions with nucleic acid of molecular clone ZVH14 (ATCC Accession No. 40,247); and further wherein said first nucleic acid does not hybridize under said stringent conditions with the nucleic acid of:

(a) Epstein-Barr virus;
   (b) human cytomegalovirus (CMV);
   (c) Herpes Simplex virus (HSV);
   (d) Varicella-Zoster virus (VZV); or
   (e) Herpes virus saimiri.

* * * * *